(12) United States Patent
Vanney

(10) Patent No.: US 7,789,877 B2
(45) Date of Patent: Sep. 7, 2010

(54) ABLATION CATHETER ELECTRODE ARRANGEMENT

(75) Inventor: Guy Vanney, Blaine, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1044 days.

(21) Appl. No.: 10/613,794

(22) Filed: Jul. 2, 2003

(65) Prior Publication Data

US 2005/0004440 A1  Jan. 6, 2005

(51) Int. Cl.
*A61B 18/18* (2006.01)
*A61M 31/00* (2006.01)

(52) U.S. Cl. .................... 606/41; 604/95.04

(58) Field of Classification Search .......... 606/41, 606/45–50; 600/434, 585; 604/95.04, 523
See application file for complete search history.

(56) References Cited

U.S. PATENT DOCUMENTS

| | | | |
|---|---|---|---|
| 3,773,034 A * | 11/1973 | Burns et al. ............... | 600/434 |
| 3,867,945 A | 2/1975 | Long | |
| 4,033,331 A | 7/1977 | Guss et al. | |
| 4,117,836 A | 10/1978 | Erikson | |
| 4,244,362 A | 1/1981 | Anderson | |
| 4,403,985 A * | 9/1983 | Boretos ............... | 604/528 |
| 4,445,892 A | 5/1984 | Hussein et al. | |
| 4,500,529 A | 2/1985 | Shanklin, Jr. et al. | |
| 4,558,155 A | 12/1985 | Shanklin, Jr. et al. | |
| 4,569,347 A | 2/1986 | Frisbie | |
| 4,581,017 A | 4/1986 | Sahota | |
| 4,641,649 A | 2/1987 | Walinsky et al. | |
| 4,705,517 A | 11/1987 | DiPisa, Jr. | |
| 4,721,117 A | 1/1988 | Mar et al. | |
| 4,729,384 A | 3/1988 | Bazenet | |
| 4,790,331 A | 12/1988 | Okeda et al. | |
| 4,810,244 A | 3/1989 | Allen | |
| 4,838,879 A | 6/1989 | Tanabe et al. | |
| 4,867,174 A | 9/1989 | Skribiski | |

(Continued)

FOREIGN PATENT DOCUMENTS

DE      40 01 086      7/1991

(Continued)

OTHER PUBLICATIONS

Cox, J. L. et al., Electrophysiology, Pacing and Arrhythmia, "Operations for Atrial Fibrillation", Clin. Cardiol. vol. 14, pp. 827-834 (1991).

(Continued)

*Primary Examiner*—Michael Peffley
(74) *Attorney, Agent, or Firm*—Wiley Rein LLP

(57) ABSTRACT

An ablation catheter employing a continuous or nearly continuous flexible electrode arrangement. In one implementation, the flexible electrode include at least one electrode defining a saw tooth pattern. In another implementation, the flexible electrode is arranged in an interlaced pattern. Generally, the flexible electrodes are configured to adapt to the change in shape of the portion of the catheter that the electrode is connected with. Moreover, the flexible electrodes are arranged to provide a continuous or nearly continuous lesion of the target tissue. In some implementations, the flexible electrode may be connected with the catheter in a biased configuration, and as such may assist in changing the shape of a curve in the catheter.

20 Claims, 15 Drawing Sheets

U.S. PATENT DOCUMENTS

| | | |
|---|---|---|
| 4,882,777 A | 11/1989 | Narula |
| 4,883,058 A | 11/1989 | Ruiz |
| 4,898,591 A | 2/1990 | Jang et al. |
| 4,911,163 A | 3/1990 | Fina |
| 4,917,102 A | 4/1990 | Miller et al. |
| 4,935,017 A | 6/1990 | Sylvanowicz |
| 4,945,912 A | 8/1990 | Langberg |
| 4,955,377 A | 9/1990 | Lennox et al. |
| 4,969,875 A | 11/1990 | Ichikawa |
| 4,988,698 A | 1/1991 | Kato et al. |
| 5,002,532 A | 3/1991 | Gaiser et al. |
| 5,016,640 A | 5/1991 | Ruiz |
| 5,100,388 A | 3/1992 | Behl et al. |
| 5,103,804 A | 4/1992 | Abele et al. |
| 5,106,360 A | 4/1992 | Ishiwara et al. |
| 5,120,323 A | 6/1992 | Shockey et al. |
| 5,123,421 A * | 6/1992 | Sinofsky ............... 600/585 |
| 5,147,315 A | 9/1992 | Weber |
| 5,162,911 A | 11/1992 | Burrage |
| 5,171,232 A | 12/1992 | Castillo et al. |
| 5,172,699 A | 12/1992 | Svenson et al. |
| 5,209,229 A | 5/1993 | Gilli |
| 5,215,540 A | 6/1993 | Anderhub |
| 5,215,989 A | 6/1993 | Baldwin et al. |
| 5,222,501 A | 6/1993 | Ideker et al. |
| 5,228,442 A | 7/1993 | Imran |
| 5,231,994 A | 8/1993 | Harmjanz |
| 5,231,995 A | 8/1993 | Desai |
| 5,242,441 A | 9/1993 | Avitall |
| 5,246,007 A | 9/1993 | Frisbie et al. |
| 5,246,438 A | 9/1993 | Langberg |
| 5,256,141 A | 10/1993 | Gencheff et al. |
| 5,263,493 A | 11/1993 | Avitall |
| 5,267,982 A | 12/1993 | Sylvanowicz |
| 5,271,392 A | 12/1993 | Ferek-Petric |
| 5,279,546 A | 1/1994 | Mische et al. |
| 5,281,213 A | 1/1994 | Milder et al. |
| 5,281,217 A | 1/1994 | Edwards et al. |
| 5,281,218 A | 1/1994 | Imran |
| 5,282,836 A | 2/1994 | Kreyenhagen et al. |
| 5,286,866 A | 2/1994 | Carr et al. |
| 5,287,858 A | 2/1994 | Hammerslag et al. |
| 5,290,229 A | 3/1994 | Paskar |
| 5,293,868 A | 3/1994 | Nardella |
| 5,295,493 A | 3/1994 | Radisch, Jr. |
| 5,299,574 A | 4/1994 | Bower |
| 5,304,131 A | 4/1994 | Paskar |
| 5,304,214 A | 4/1994 | DeFord et al. |
| 5,312,355 A | 5/1994 | Lee |
| 5,322,509 A | 6/1994 | Rickerd |
| 5,348,554 A | 9/1994 | Imran et al. |
| 5,366,490 A | 11/1994 | Edwards et al. |
| 5,391,147 A | 2/1995 | Imran et al. |
| 5,405,376 A | 4/1995 | Mulier et al. |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,433,729 A | 7/1995 | Adams et al. |
| 5,450,846 A | 9/1995 | Goldreyer |
| 5,462,529 A | 10/1995 | Simpson et al. |
| 5,468,239 A | 11/1995 | Tanner et al. |
| 5,472,441 A | 12/1995 | Edwards et al. |
| 5,476,495 A | 12/1995 | Kordis et al. |
| 5,478,330 A | 12/1995 | Imran et al. |
| 5,484,412 A | 1/1996 | Pierpont |
| 5,497,774 A | 3/1996 | Swartz et al. |
| 5,499,981 A * | 3/1996 | Kordis ............... 606/41 |
| 5,536,247 A | 7/1996 | Thornton |
| 5,540,679 A | 7/1996 | Fram et al. |
| 5,542,928 A | 8/1996 | Evans et al. |
| 5,545,161 A | 8/1996 | Imran |
| 5,564,440 A | 10/1996 | Swartz et al. |
| 5,571,088 A | 11/1996 | Lennox et al. |
| 5,575,766 A | 11/1996 | Swartz et al. |
| 5,575,772 A | 11/1996 | Lennox |
| 5,584,872 A | 12/1996 | LaFontaine et al. |
| 5,588,961 A | 12/1996 | Leone et al. |
| 5,588,964 A | 12/1996 | Imran et al. |
| 5,599,307 A | 2/1997 | Bacher et al. |
| 5,609,151 A | 3/1997 | Muiler et al. |
| 5,624,439 A | 4/1997 | Edwards et al. |
| 5,628,316 A | 5/1997 | Swartz et al. |
| 5,640,955 A | 6/1997 | Ockuly et al. |
| 5,643,231 A | 7/1997 | Lurie et al. |
| 5,656,029 A | 8/1997 | Imran et al. |
| 5,658,278 A | 8/1997 | Imran et al. |
| 5,676,693 A | 10/1997 | LaFontaine |
| 5,680,860 A | 10/1997 | Imran |
| 5,681,308 A | 10/1997 | Edwards et al. |
| 5,697,927 A | 12/1997 | Imran et al. |
| 5,722,400 A | 3/1998 | Ockuly et al. |
| 5,746,495 A | 5/1998 | Klamm |
| 5,785,706 A | 7/1998 | Bednarek |
| 5,792,105 A | 8/1998 | Lin et al. |
| 5,792,140 A | 8/1998 | Tu et al. |
| 5,797,905 A | 8/1998 | Fleischman et al. |
| 5,800,482 A | 9/1998 | Pomeranz et al. |
| 5,807,306 A | 9/1998 | Shapland et al. |
| 5,807,395 A | 9/1998 | Mulier et al. |
| 5,814,029 A | 9/1998 | Hassett |
| 5,842,984 A | 12/1998 | Avitall |
| 5,843,152 A | 12/1998 | Tu et al. |
| 5,846,223 A | 12/1998 | Swartz et al. |
| 5,860,974 A | 1/1999 | Abele |
| 5,876,398 A | 3/1999 | Mulier et al. |
| 5,876,399 A | 3/1999 | Chia et al. |
| 5,882,346 A | 3/1999 | Pomeranz et al. |
| 5,893,884 A | 4/1999 | Tu |
| 5,895,417 A | 4/1999 | Pomeranz et al. |
| 5,906,613 A | 5/1999 | Mulier et al. |
| 5,910,129 A | 6/1999 | Koblish et al. |
| 5,913,854 A * | 6/1999 | Maguire et al. ............... 606/41 |
| 5,913,856 A | 6/1999 | Chia et al. |
| 5,916,213 A | 6/1999 | Haissaguerre et al. |
| 5,919,188 A | 7/1999 | Shearon et al. |
| 5,921,924 A | 7/1999 | Avitali |
| 5,938,659 A | 8/1999 | Tu et al. |
| 5,938,660 A | 8/1999 | Swartz et al. |
| 5,971,968 A | 10/1999 | Tu et al. |
| 5,971,983 A | 10/1999 | Lesh |
| 5,980,516 A | 11/1999 | Mulier et al. |
| 5,993,462 A | 11/1999 | Pomeranz et al. |
| 5,997,532 A | 12/1999 | McLaughlin et al. |
| 6,001,085 A | 12/1999 | Lurie et al. |
| 6,001,093 A * | 12/1999 | Swanson et al. ............... 606/41 |
| 6,004,269 A | 12/1999 | Crowley et al. |
| 6,010,500 A | 1/2000 | Sherman et al. |
| 6,012,457 A | 1/2000 | Lesh |
| 6,015,407 A | 1/2000 | Rieb et al. |
| 6,016,809 A | 1/2000 | Mulier et al. |
| 6,023,638 A | 2/2000 | Swanson |
| 6,024,740 A | 2/2000 | Lesh et al. |
| 6,032,077 A | 2/2000 | Pomeranz |
| 6,048,329 A | 4/2000 | Thompston et al. |
| 6,063,080 A | 5/2000 | Nelson et al. |
| 6,068,629 A | 5/2000 | Haissaguerre et al. |
| 6,068,653 A | 5/2000 | LaFontaine |
| 6,071,274 A | 6/2000 | Thompston et al. |
| 6,071,279 A | 6/2000 | Whayne et al. |
| 6,076,012 A | 6/2000 | Swanson et al. |
| 6,080,151 A | 6/2000 | Swartz et al. |
| 6,097,976 A | 8/2000 | Yang et al. |

| | | |
|---|---|---|
| 6,117,101 A | 9/2000 | Diederich et al. |
| 6,119,041 A | 9/2000 | Pomeranz et al. |
| 6,120,476 A | 9/2000 | Fung et al. |
| 6,120,500 A | 9/2000 | Bednarek et al. |
| 6,138,043 A | 10/2000 | Avitall |
| 6,156,018 A | 12/2000 | Hassett |
| 6,164,283 A | 12/2000 | Lesh |
| 6,168,594 B1 | 1/2001 | LaFontaine et al. |
| 6,171,275 B1 | 1/2001 | Webster, Jr. |
| 6,171,277 B1 | 1/2001 | Ponzi |
| 6,171,306 B1 * | 1/2001 | Swanson et al. ............ 606/41 |
| 6,183,463 B1 | 2/2001 | Webster, Jr. |
| 6,203,525 B1 | 3/2001 | Whayne et al. |
| 6,210,406 B1 | 4/2001 | Webster |
| 6,212,426 B1 | 4/2001 | Swanson |
| 6,217,573 B1 | 4/2001 | Webster |
| 6,217,574 B1 | 4/2001 | Webster |
| 6,217,576 B1 | 4/2001 | Tu et al. |
| 6,235,021 B1 | 5/2001 | Sieben |
| 6,235,025 B1 | 5/2001 | Swartz et al. |
| 6,238,393 B1 | 5/2001 | Mulier et al. |
| 6,241,722 B1 | 6/2001 | Dobak et al. |
| 6,241,727 B1 | 6/2001 | Tu et al. |
| 6,241,754 B1 | 6/2001 | Swanson et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,264,654 B1 | 7/2001 | Swartz et al. |
| 6,290,697 B1 | 9/2001 | Tu et al. |
| 6,305,378 B1 | 10/2001 | Lesh |
| 6,308,091 B1 | 10/2001 | Avitall |
| 6,325,797 B1 | 12/2001 | Stewart et al. |
| 6,330,473 B1 | 12/2001 | Swanson et al. |
| 6,371,955 B1 | 4/2002 | Fuimaono et al. |
| 6,383,151 B1 | 5/2002 | Diederich et al. |
| 6,402,746 B1 | 6/2002 | Whayne et al. |
| 6,409,722 B1 | 6/2002 | Hoey et al. |
| 6,416,511 B1 | 7/2002 | Lesh et al. |
| 6,447,507 B1 | 9/2002 | Bednarek et al. |
| 6,454,758 B1 | 9/2002 | Thompson et al. |
| 6,454,766 B1 | 9/2002 | Swanson et al. |
| 6,503,247 B2 | 1/2003 | Swartz et al. |
| 6,522,930 B1 | 2/2003 | Schaer et al. |
| 6,526,302 B2 | 2/2003 | Hassett |
| 6,540,744 B2 | 4/2003 | Hassett et al. |
| 6,540,755 B2 | 4/2003 | Ockuly et al. |
| 6,600,956 B2 * | 7/2003 | Maschino et al. ........... 607/118 |
| 6,605,087 B2 | 8/2003 | Swartz et al. |
| 6,607,520 B2 | 8/2003 | Keane |
| 6,620,155 B2 | 9/2003 | Underwood et al. |
| 6,702,811 B2 | 3/2004 | Stewart et al. |
| 6,872,205 B2 | 3/2005 | Lesh et al. |
| 6,942,661 B2 | 9/2005 | Swanson |
| 6,984,232 B2 | 1/2006 | Vanney et al. |
| 7,025,766 B2 | 4/2006 | Whayne et al. |
| 7,101,362 B2 * | 9/2006 | Vanney ....................... 604/523 |
| 7,122,034 B2 | 10/2006 | Belhe et al. |
| 7,419,486 B2 | 9/2008 | Kampa |
| 2002/0072741 A1 | 6/2002 | Sliwa et al. |
| 2003/0130713 A1 | 7/2003 | Stewart et al. |
| 2004/0143253 A1 | 7/2004 | Vanney et al. |
| 2005/0004565 A1 | 1/2005 | Vanney et al. |
| 2006/0111708 A1 | 5/2006 | Vanney et al. |
| 2006/0287650 A1 | 12/2006 | Cao et al. |
| 2007/0005051 A1 | 1/2007 | Kampa |

FOREIGN PATENT DOCUMENTS

| | | |
|---|---|---|
| EP | A 656217 | 6/1995 |
| EP | A 670168 | 9/1995 |
| WO | WO 92/12754 | 8/1992 |
| WO | WO 92/19307 | 11/1992 |
| WO | WO 96/00042 | 1/1996 |
| WO | WO 97/16127 | 5/1997 |
| WO | 99/48421 A | 9/1999 |

OTHER PUBLICATIONS

Cox, J. L. et al., "The Surgical Treatment of Atrial Fibrillation", The Journal of Thoracic and Cardiovascular Surgery, vol. 101, No. 4, pp. 569-592 (Apr. 1991).

Cox, J. L. et al., "The Surgical Treatment of Atrial Fibrillation", The Journal of Thoracic and Cardiovascular Surgery, vol. 101, No. 4, pp. 406-426 (Mar. 1991).

Falk, R. H. et al., Atrial Fibrillation Mechanisms and Management, pp. 359-374 (1992).

Heinz, G. et al., "Improvement in Left Ventricular Systolic Function After Successful Radiofrequency His Bundle Ablation for Drug Refractory, Chronic Atrial Fibrillation and Recurrent Atrial Flutter", Am. J. Cordiol., vol. 69, pp. 489-492 (Feb. 15, 1992).

Huang, S. K. et al., "Closed Chest Catheter Desiccation of the Atrioventricular Junction Using Radiofrequency Energy—A New Method of Catheter Ablation", J. Am. Coll. Cardiol., vol. 9, No. 2, pp. 349-358 (Feb. 1987).

Horowitz, L. N., Current Management of Arrhythmias, pp. 373-378 (1991).

Gallagher, J. J. et al., Catheter Technique for Closed-Chest Ablation of the Atrioventricular Conduction System, N. Engl. J. Med., vol. 306, pp. 194-200 (Jan. 28, 1982).

Martin, D. et al., "Artial Fibrillation", pp. 35-59 (1994).

Saul, J. P. et al., "Catheter Ablation of Accessory Atrioventricular Pathways in Young Patients: Use of Long Vascular Sheaths, the Transseptal Approach and a Retrograde Left Posterior Parallel Approach", J. Amer. Coll. Card., vol. 21, No. 3, pp. 571-583 (Mar. 1, 1993).

Scheinman, M. M. et al., "Catheter-Induced Ablation of the Artioventricular Junction to Control Rafractory Supraventricular Arrhythmias", JAMA, vol. 248, pp. 851-855 (Aug. 20, 1982).

Swartz, J. F. et al., "Radiofrequency Endocardial Catheter Ablation of Accessory Atrioventricular Pathway Atrial Insertion Sites", Circulation, vol. 87, No. 2, pp. 487-499 (Feb. 1993).

Singer, I. et al., "Catheter Ablation for Arrhythmias", Clinical Manual of Electrophysiology, pp. 421-431 (1993).

Tracy, C. M., "Radiofrequency Catheter Ablation of Ectopic Atrial Tachycardia Using Paced Activation Sequence Mapping", J. Am. Coll. Cardiol., vol. 21, pp. 910-917 (Mar. 15, 1993).

Haissaguerre, M. et al., "Right and Left Atrial Radiofrequency Catheter Therapy of Paroxysmal Atrial Fibrillation", Journal of Cardiovascular Electrophysiology, vol. 7, No. 12, pp. 1132-1144 (Dec. 1996).

Office action mailed Jun. 8, 2007 in related U.S. Appl. No. 10/608,257.

Supplementary European Search Report for EP04703670 dated Oct. 9, 2007.

International Search Report and Written Opinion of the International Searching Authority for PCT/US07/89110 dated Jul. 7, 2008.

\* cited by examiner

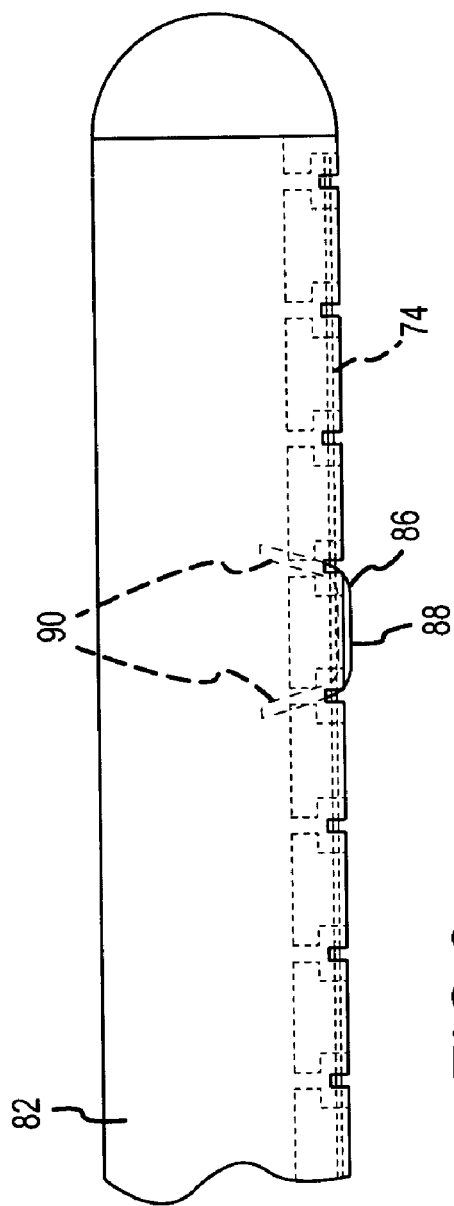
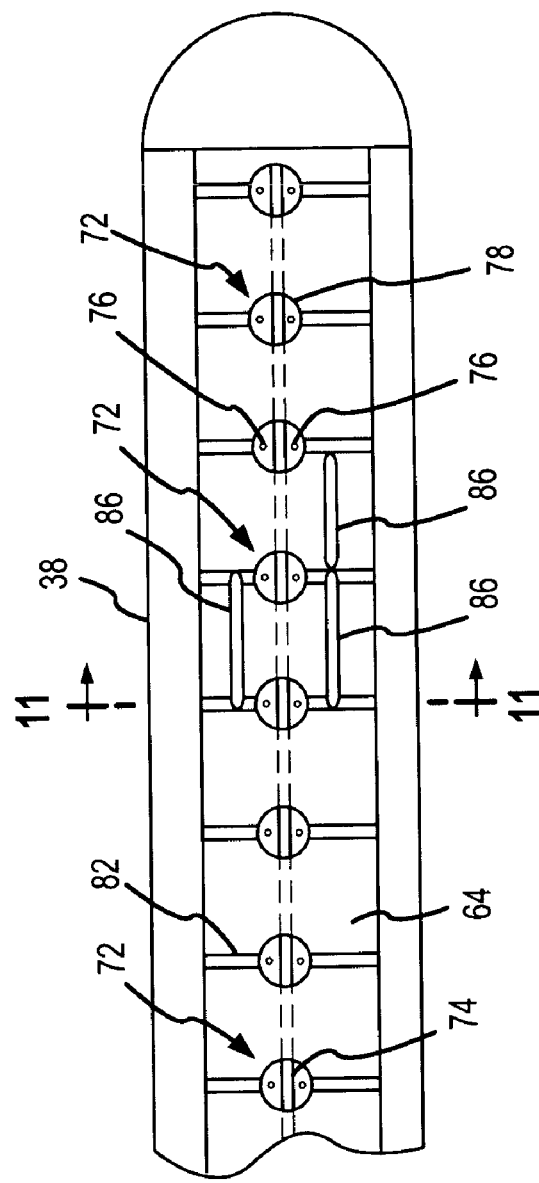
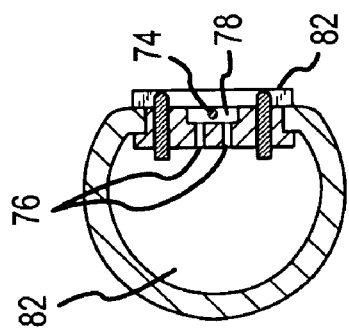
FIG. 9
FIG. 10
FIG. 11

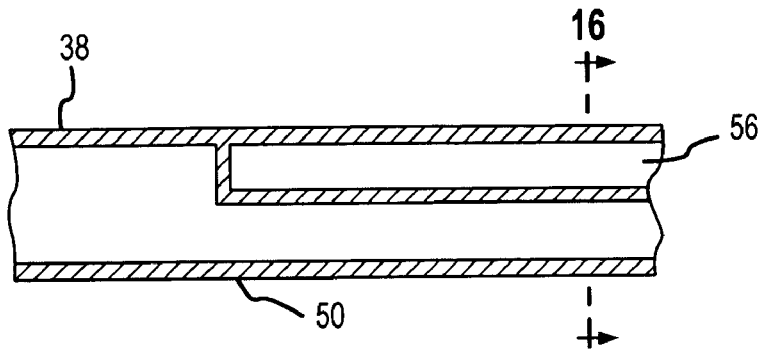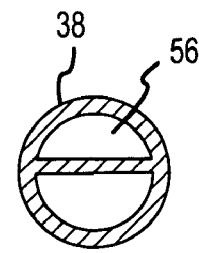
FIG.15A  FIG.16
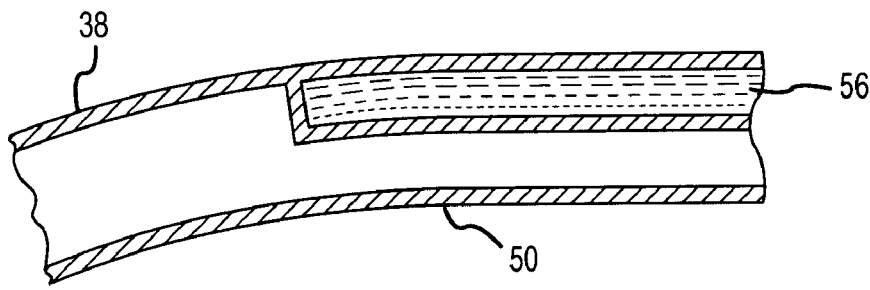
FIG.15B
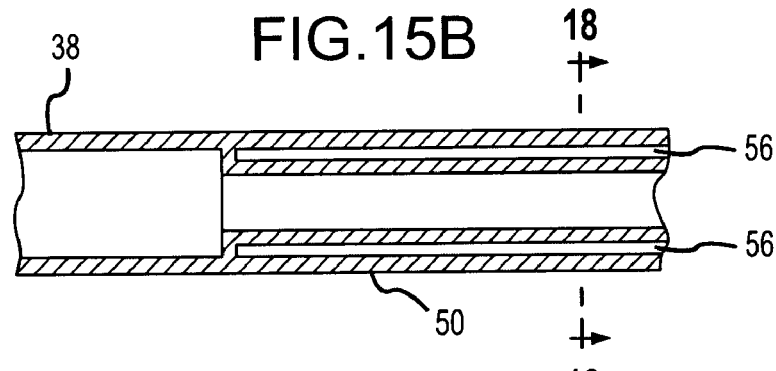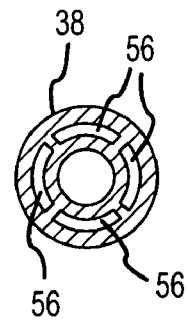
FIG.17A  FIG.18
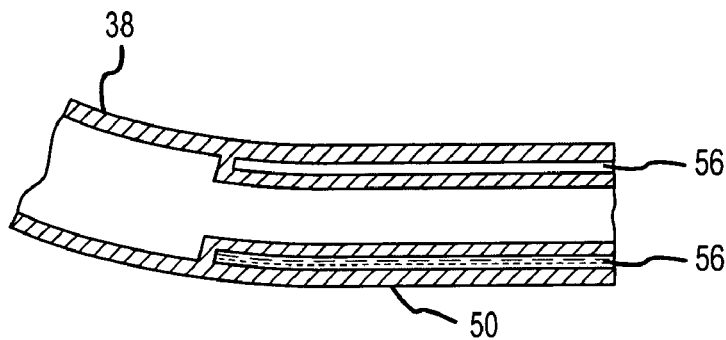
FIG.17B

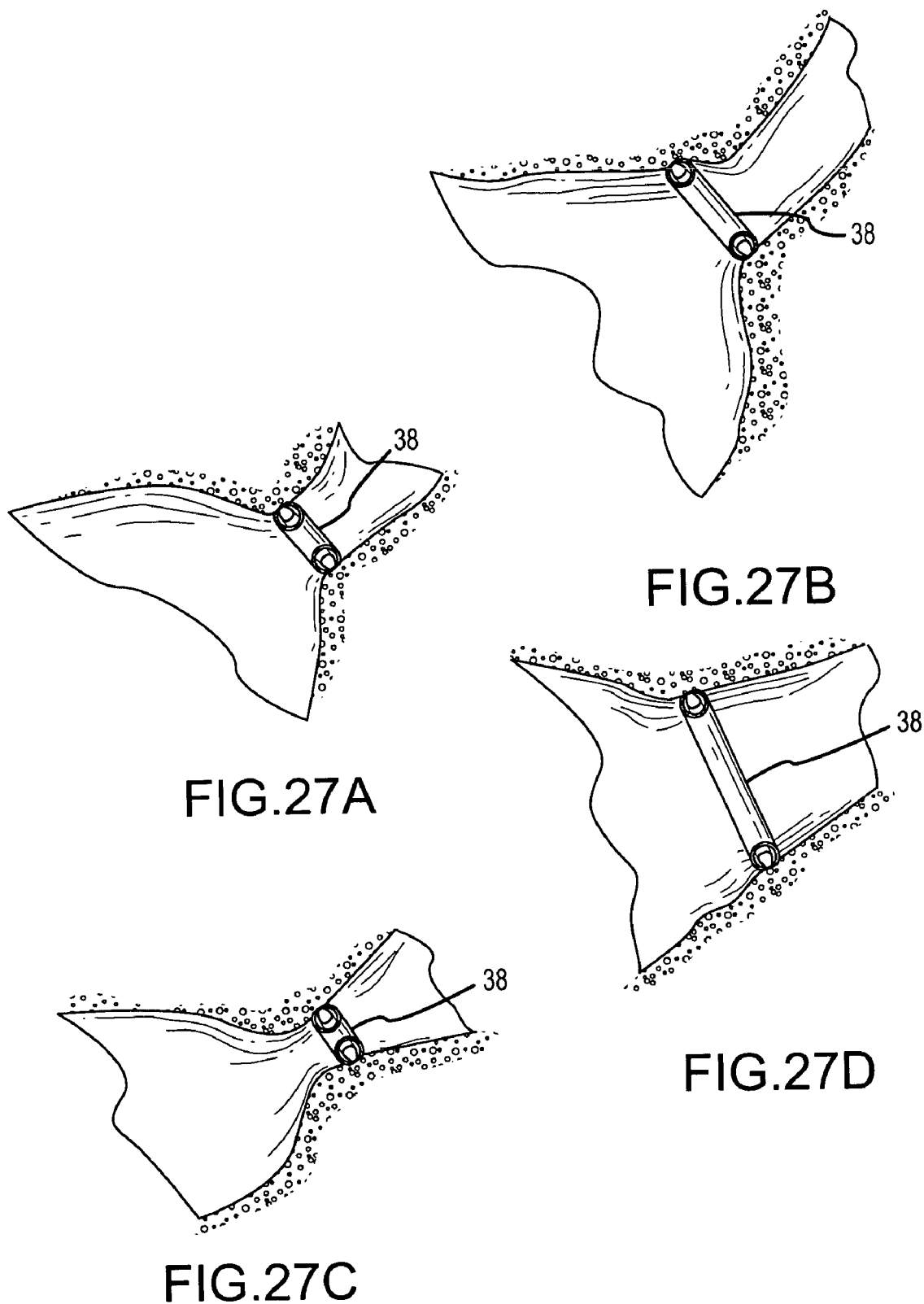

ABLATION CATHETER ELECTRODE ARRANGEMENT

BACKGROUND OF THE INVENTION a. Field of the Invention

Generally, the present invention is related to the field of ablation catheters. More particularly, aspects of the present invention involve an ablation catheter employing a continuous or partially continuous electrode adapted to provide a continuous or nearly continuous lesion at a target tissue. Aspects of the present invention also involve a steerable and shapable catheter employing fluid force to steer and change the shape of the catheter. Aspects of the present invention also involve an ablation catheter manifolding arrangement for directing ablation fluid to a target tissue.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" utilizes a catheter to convey an electrical energy to a selected location within the human body to create necrosis, which is commonly referred to as ablation of cardiac tissue. Another procedure oftentimes referred to as "mapping" utilizes a catheter with sensing electrodes to monitor various forms of electrical activity in the human body.

Catheters are used increasingly for medical procedures involving the human heart. As illustrated in FIG. 1, a typical human heart 10 includes a right ventricle 12, a right atrium 14, a left ventricle 16 and a left atrium 18. The right atrium is in fluid communication with the superior vena cava 20 and the inferior vena cava 22. The interatrial septum 24 separates the right atrium from the left atrium. The tricuspid valve 26 contained within the atrioventricular septum provides a fluid flow path between the right atrium with the right ventricle. On the inner wall of the right atrium where it is connected with the left atrium is a thin walled, recessed area, referred to as the fossa ovalis 28. Between the fossa ovalis and the tricuspid valve is the opening or ostium for the coronary sinus 30. The coronary sinus is the large epicardial vein which accommodates most of the venous blood which drains from the myocardium into the right atrium.

In a normal heart, contraction and relaxation of the heart muscle (myocardium) takes place in an organized fashion as electrochemical signals pass sequentially through the myocardium from the sinoatrial (SA) node (not shown) located in the right atrium to the atrialventricular (AV) node (not shown) and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve 26 through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atrium which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including the following: (1) an irregular heart rate, which causes a patient discomfort and anxiety, (2) loss of synchronous atrioventricular contractions which compromises cardiac hemodynamics resulting in varying levels of congestive heart failure, and (3) stasis of blood flow, which increases the vulnerability to thromboembolism. It is sometimes difficult to isolate a specific pathological cause for the atrial fibrillation although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate atrial fibrillations.

In some conventional ablation procedures, the ablation catheter includes a single distal electrode secured to the tip of the ablation catheter to produce small lesions wherever the tip contacts the tissue. To produce a linear lesion, the tip may be dragged slowly along the tissue during energy application. Increasingly, however, cardiac ablation procedures utilize multiple electrodes affixed to the catheter body to form multiple lesions.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

Moreover, effective ablation procedures are sometimes quite difficult because of the need for an extended linear lesion, sometimes as long as about three inches to five inches (approximately eight centimeters to twelve centimeters). To consistently produce such a linear lesion of this length within a wide variety of cardiac anatomies. In some instances, stray electrical signals find a pathway down the pulmonary veins 32 and into the left atrium. In these instances, it may be desirable to produce a circumferential lesion at the ostium 34 to one or more of the pulmonary veins or within one or more of the pulmonary veins. The pulmonary veins may reach a circumference of up to about 90 millimeters; thus, about a 90 millimeter circumferential lesion would be desirable to completely block stray signals from traveling down the pulmonary vein and into the left atrium.

Besides the difficulty in achieving an adequate lesion at the target tissue, it is also difficult to properly guide the catheter through the body to the target tissue and to change the shape of the catheter so that the ablation electrode is properly positioned at or against the target tissue. For instance, to guide a catheter into the left atrium of the heart for an ablation procedure at a pulmonary vein, a catheter oftentimes is fed into a vein in the right leg routed up to the right atrium of the heart, turned to the right and pressed through the septum between the left and right atrium to gain access to the left atrium. Once in the left atrium, the catheter must be further maneuvered to the appropriate pulmonary vein. In such a maneuvering of the catheter, numerous turns must be achieved to place the catheter at the ultimate target vein.

SUMMARY OF THE INVENTION

One implementation of an ablation catheter conforming to the present invention comprises a tubular body having a distal end region, the tubular body defining at least a partial curve along the distal end region of the tubular body, the partial curve being adapted to change curvature. In addition, at least one electrode is arranged along the at least partial curve, the at least one electrode being adapted to change curvature along with the at least partial curve along the distal end region of the tubular body. The electrode may comprise at least one electrode strand arranged in a flexible and/or resilient configuration arranged in a saw tooth pattern. The electrode may be placed or connected with the catheter anywhere along the shaft. For example, the electrode may be arranged along the outside of the curved portion of the shaft, along the inside of the curved portion of the shaft, along the top of the curved portion of the shaft, etc.

The flexible electrode arrangement may further be provided in an elastically deformable configuration. In such a configuration, the electrode may be biased when connected with the catheter. When biased, the electrode may affect the curvature of the shaft. The curvature of the shaft, in some implementations, may define an open loop, a closed loop, or other generally arcutate shapes.

In an alternative configuration, the flexible electrode may be arranged in an interlaced or interwoven pattern along some portion of the shaft, such as along some part of the curved portion of the shaft, e.g., along the inside, the outside, or the top of the curved portion the shaft. In an interlaced arrangement, the electrode strand may be intermittently exposed along the shaft. Particularly, at least one electrode strand may define a first length of the at least one strand, the first length defining intermittently exposed sections of the at least one electrode strand; and the at least one electrode strand may further define a second length of the at least one strand, the second length defining intermittently exposed sections of the at least one electrode strand. The first length of the at least one strand and the second length of the at least one strand cooperate to define a generally continuously exposed segment of the at least one strand.

A more detailed explanation of the invention is provided in the following description and claims, and is illustrated in the accompanying drawings.

BRIEF DESCRIPTION OF THE DRAWINGS

FIG. 9 is a partial top view of a distal portion of a shapable catheter, in accordance with one embodiment of the present invention.

FIG. 10 is a partial side view of the catheter shown in FIG. 9.

FIG. 11 is a section view of the catheter taken along line 11-11 of FIG. 10.

FIGS. 15A and 15B are longitudinal section views of one example of a catheter including an actuating lumen.

FIG. 16 is a section view of the catheter of FIG. 15A taken along line 16-16 of FIG. 15A.

FIGS. 17A and 17B are longitudinal section views of one example of a catheter including a plurality of actuating lumens.

FIG. 18 is a section view of the catheter of FIG. 17A taken along line 18-18 of FIG. 17A.

FIG. 27A is a representative section view of the looped portion of the steerable ablation catheter and braided electrode pressed against the walls of the pulmonary vein.

FIG. 27B is a representative section view of the looped portion of the steerable ablation catheter and braided electrode positioned partially against the wall of the pulmonary vein and partially against the ostium to the pulmonary vein.

FIG. 27C is a representative section view of the looped portion of the steerable ablation catheter and ablation electrode pressed against a somewhat conically shaped wall of the pulmonary vein.

FIG. 27D is a representative section view of the looped portion of the steerable ablation catheter and braided electrode pressed against the walls of a pulmonary vein adjacent a relatively large ostium thereto.

DESCRIPTION OF THE PREFERRED EMBODIMENTS

Figure 1:
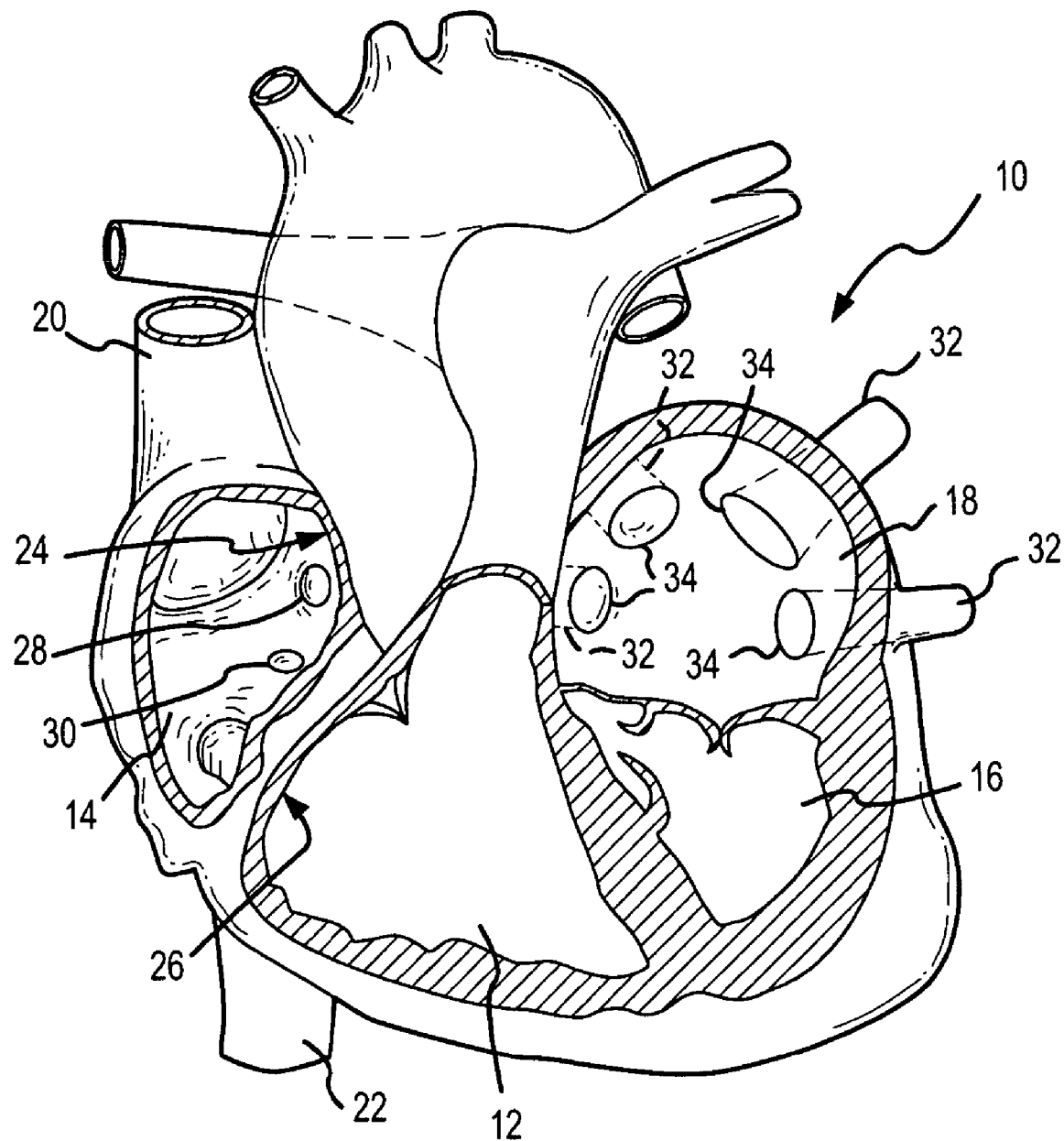
FIG. 1 is a partial cut away diagram of a human heart.

Aspects of the present invention involve an ablation catheter employing a continuous or nearly continuous electrode for delivering a continuous or nearly continuous lesion at a target tissue. In an ablation catheter configured particularly for an ablation procedure at a pulmonary vein in or at the left atrium, the catheter may define a curve, such as a partial or complete loop, at its distal end region. In one particular implementation, the electrode includes an elastically deformable or flexible electrode strand arranged in a saw tooth pattern. The flexible electrode is connected with the catheter along the outside curve of the loop. In another particular implementation, the electrode includes an electrode strand connected with the outside curve of the loop in an interlaced or interwoven pattern. The catheter may include a mechanism whereby the loop shape may be expanded or contracted in order to maneuver the loop into or at a pulmonary vein and change the shape of the loop so that the electrode along the outside curve of the loop is pressed against the walls of the target vein.

In the flexible electrode catheter implementations the electrode may define a narrow width along some portion of the curve portion of the catheter. Thus, when pressed against the target tissue, most or all of the electrode will be exposed to the target tissue and not exposed to the surrounding blood. Moreover, in either implementation, the electrode configuration allows the electrode to be fixed at some point or points along the curve and also expand or contract with the changing curve of the loop.

Aspects of the present invention also involve a steerable and shapable catheter that employs fluid induced force in a lumen to change the shape of the catheter for a procedure, steer the catheter as it is being directed toward some location in the body, or conduct other procedures. In one particular arrangement, the tubular body of the catheter defines one or more preset curves and defines or includes at least one actuating lumen connected with or integral with the tubular body. By introducing, increasing, decreasing, or eliminating a fluid material in the actuating lumen, a force that changes the shape of the catheter is introduced, increased, decreased, or eliminated, respectively. Thus, by managing the proper amount of fluid force or pressure in the actuating lumen, the catheter shape may be manipulated into a particular shape and thereby maneuvered into a desired location or arranged into a desired shape for a procedure at the target tissue.

The implementations of a shapable catheter discussed herein are described with respect to an arrangement particularly suited for guiding the catheter to a pulmonary vein using a transeptal approach and performing an ablation procedure at one of the pulmonary veins in the left atrium. As such, one particular configuration of a catheter in accordance with the present invention includes an ablation region. As used herein, the phrase "ablation region" is meant to refer to the section of an ablation catheter that includes ablation structure, such as electrodes and manifolding, and/or particular shaping elements, preset curves, and the like implemented to facilitate ablation of target tissue. However, a shapable catheter conforming to the present invention may be employed in an ablation arrangement, with or without metal electrodes, or in a mapping arrangement, or any other arrangement requiring a catheter that may be guided to a target location within the body to perform any number of medical procedures. As such, aspects of the present invention is not limited to providing a shapable catheter suited only for ablation procedures at the pulmonary veins, but is meant to encompass any shapable and steerable catheter arrangement employing fluid force to steer or shape the catheter regardless of any particular procedure the catheter is used for.

The shapable and steerable catheter may employ a continuous electrode for delivering a continuous or nearly continuous lesion at a target tissue as introduced above and discussed in more detail below. Alternatively, the shapable and steerable catheter may employ a manifolding arrangement in accordance with one embodiment of the present invention. The manifold arrangement is adapted to convey energized ablation fluid to a target tissue. In one particular arrangement, the catheter includes a tubular body defining a curved loop region along the distal end ablation region of the catheter. The loop region is particularly suited for ablation procedures at a pulmonary vein at the left atrium. The tubular body includes an ablation fluid supply lumen adapted to provide ablation fluid to the looped portion of the catheter. A plurality of manifold arrangements are provided along the loop region of the catheter. The manifolds provide a conduit for directing ablation fluid from the ablation fluid supply lumen fairly uniformly through each manifold around the loop.

Figure 2:
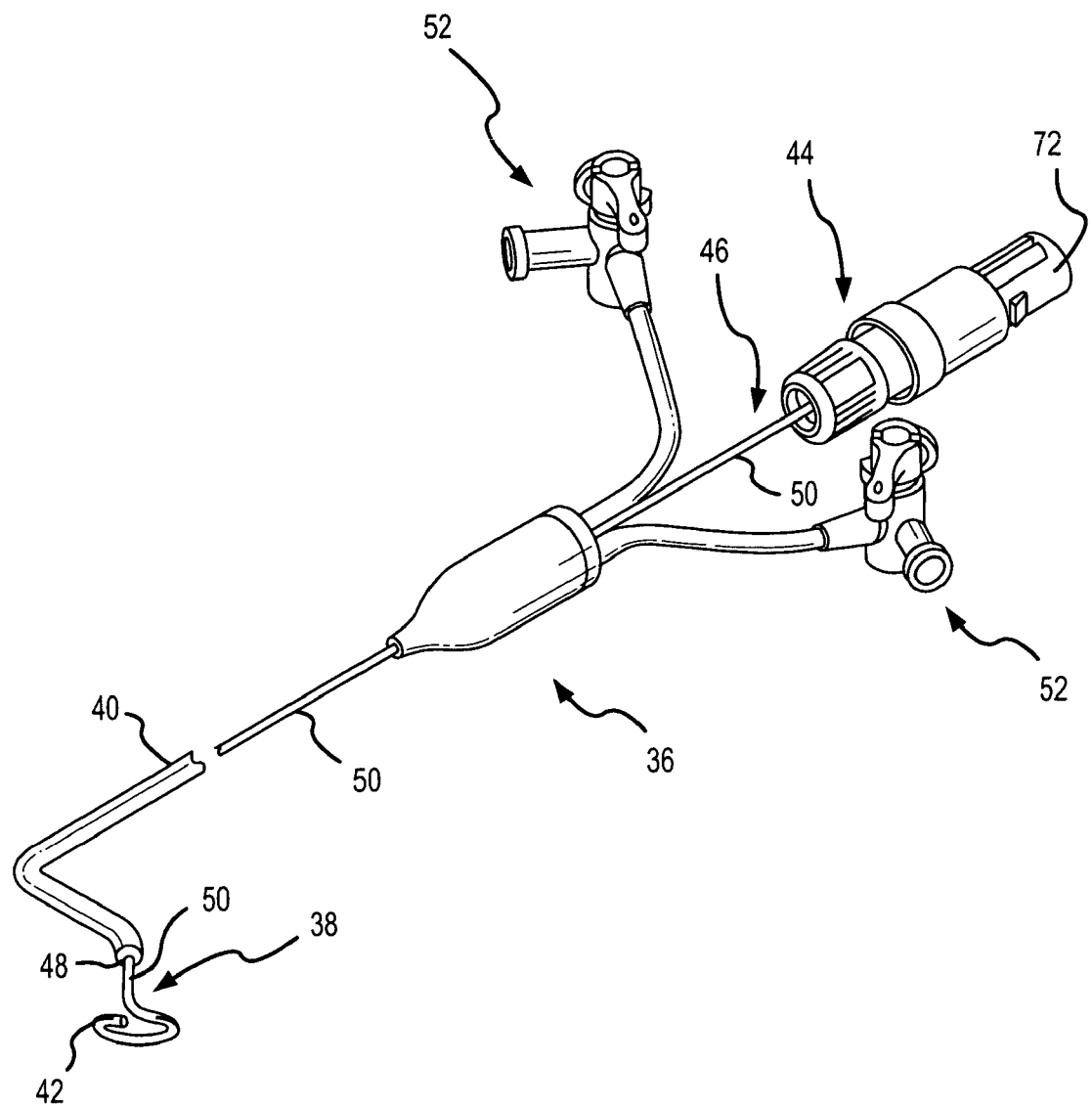
FIG. 2 is an isometric view of a shapable ablation catheter and associated catheter control system, in accordance with one embodiment of the present invention.

FIG. 2 illustrates one embodiment of a catheter ablation system 36 with a shapable ablation catheter 38 extending from the distal end portion of a sheath 40 of a guiding introducer. As used herein and commonly used in the art, the term "distal" is used generally to refer to components of the catheter system, such as an ablation region 42 of the catheter 38, that is located or generally orientated toward the heart or other target tissue when the catheter is in use. On the other hand, the term "proximal" is used generally to refer to components or portions of the catheter, such as a connector 44, that are located or generally orientated away from or opposite the heart or other target tissue when the catheter is in use.

The sheath 40 is a tubular structure defining at least one lumen 48 or longitudinal channel. The sheath is used in conjunction with the catheter to introduce and guide and catheter to the target tissue. The catheter, however, may be used alone or with other guiding and introducing type devices depending on the particular procedure being performed. As shown in FIG. 2, the catheter includes a tubular body or shaft 50 extending from the connector, through the sheath, and out of the lumen at the distal end of the sheath of the introducer. In one implementation, the sheath and shaft are fabricated with a flexible resilient material. The sheath and the components of the catheter are preferably fabricated of materials suitable for use in humans, such as nonconductive polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials. Some portions of the sheath 40 and catheter 38 may be braided for enhanced stiffness. In the particular ablation system configuration of FIG. 2, the sheath 40 is configured to receive and guide the ablation catheter within the lumen 48 to the appropriate location in the heart once the sheath is pre-positioned in the appropriate location.

To pre-position the sheath 40 at the appropriate location in the heart, a dilator and a needle (not shown) are fitted within the lumen 48 of the sheath. When the dilator and needle are within the lumen, the ablation catheter 38 is not within the lumen. In an example of a procedure within the left atrium 18, the sheath and the dilator are first inserted in the femoral vein in the right leg. The sheath and dilator are then maneuvered up to the inferior vena cava 22 and into the right atrium 14. In what is typically referred to as a transseptal approach, the needle is pressed through the interatrial septum 24 between the right and left atria. Following the needle, the dilator is pressed through the small opening made by the needle. The dilator expands the opening sufficiently so that the sheath may then be pressed through the opening to gain access to the left atrium 18 and the pulmonary veins 32. With the sheath in position, the dilator is removed and the shapable catheter 38 is fed into the lumen of the sheath 40 and pushed along the sheath into the left atrium 14. When positioned in the left atrium, various procedures, such as ablation and mapping, may be performed therein.

In some implementations, the sheath, dilator, and ablation catheter are each about two to four feet long, so that they may extend from the left atrium through the body and out of the femoral vein in the right leg and be connected with various catheter ablation procedure devices such as the connector 44, one or more fluid control valves 52, and the like. A more detailed description of the process of forming an ablation at the left superior pulmonary vein is discussed below with regard to FIGS. 25 and 26. The ablation catheter system 36 is typically discussed herein with reference to procedures in the left atrium 18 in the vicinity of or within the pulmonary veins 32. The ablation catheter system, however, is not limited to such procedures, and may be used for ablation of target tissue in other areas of the heart and body.

Figure 3A:
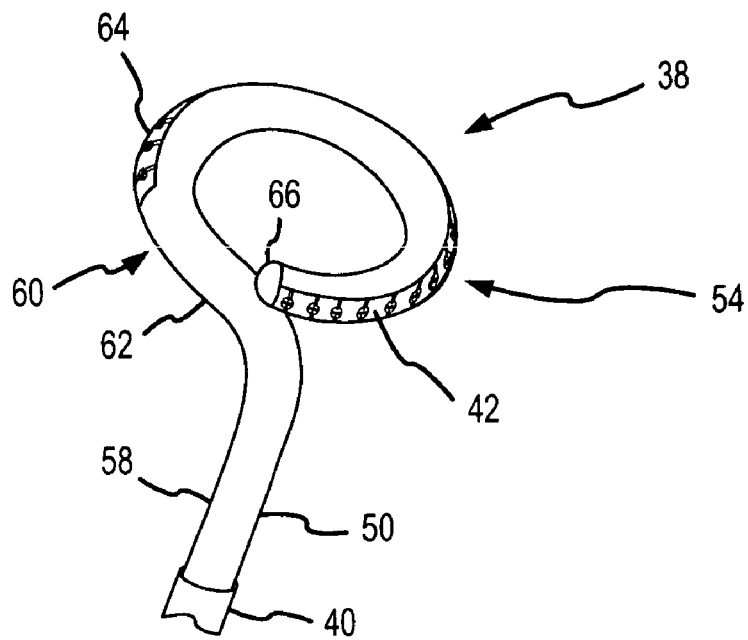
FIG. 3A is an isometric view of the distal end region of a precurved shapable ablation catheter, before introduction of a fluid into an activating lumen, in accordance with one embodiment of the present invention.
Figure 3B:
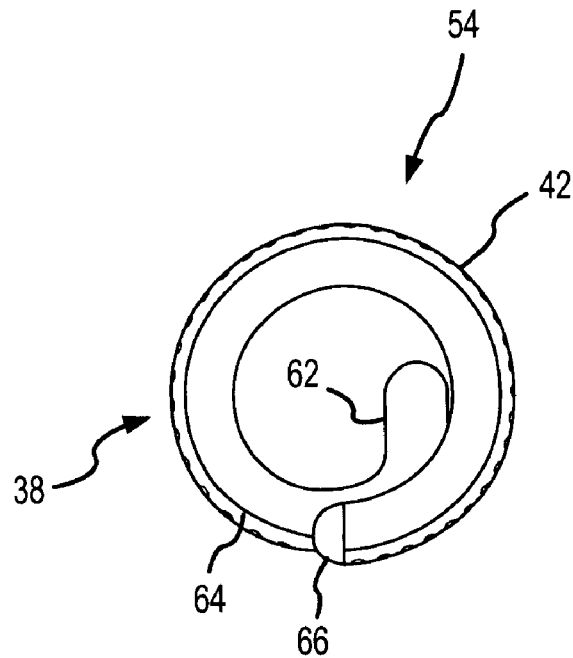
FIG. 3B is a top view of the catheter of FIG. 3A.
Figure 3C:
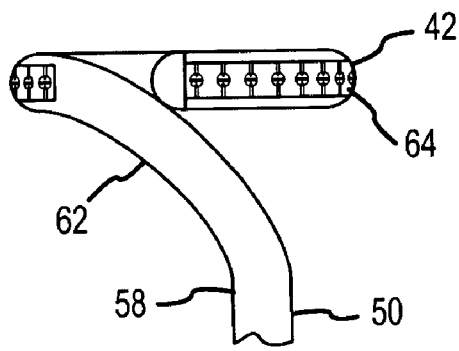
FIG. 3C is a side view of the catheter of FIG. 3A.
Figure 4A:
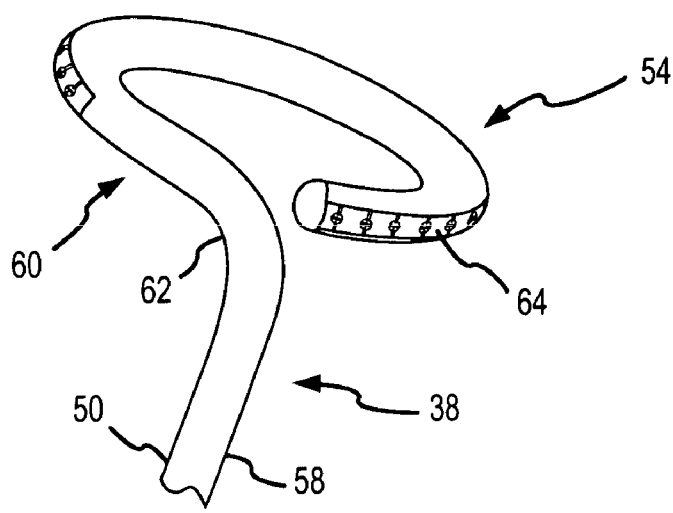
FIG. 4A is an isometric view of the distal portion of the precurved shapable ablation catheter of FIGS. 3A-3C after introduction of a fluid into the activating lumen, in accordance with one embodiment of the present invention.
Figure 4B:
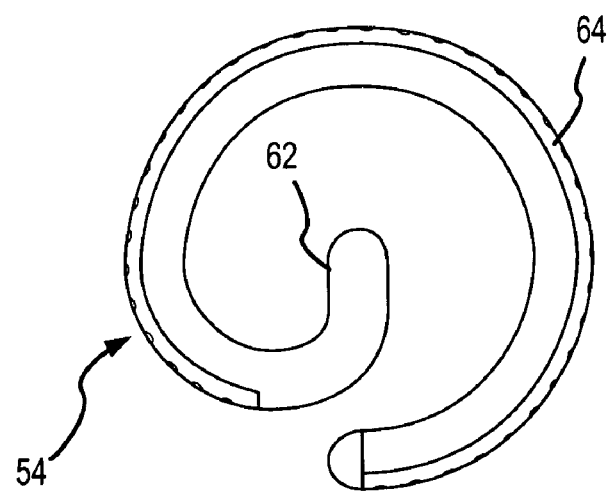
FIG. 4B is a top view of the catheter of FIG. 4A.
Figure 4C:
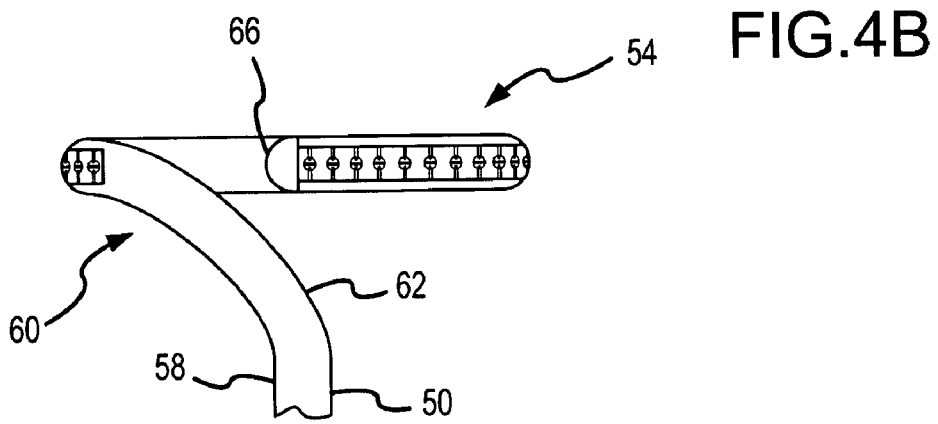
FIG. 4C is a side view of the catheter of FIG. 4A.
Figure 5:
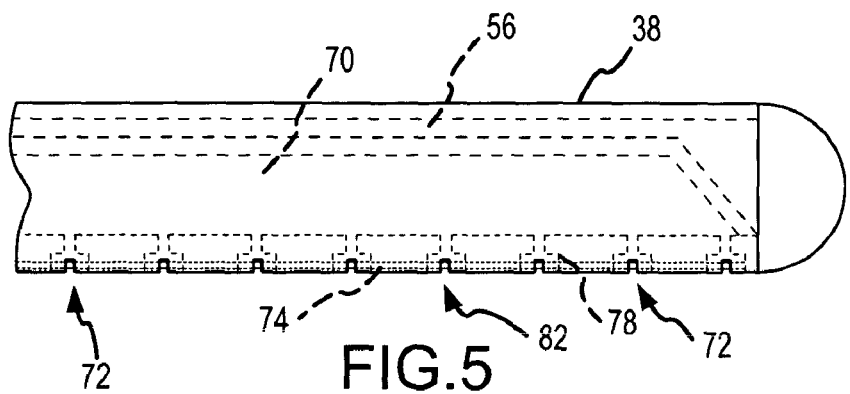
FIG. 5 is a partial top view of a distal portion of a shapable catheter, in accordance with one embodiment of the present invention.
Figures 6, 7:
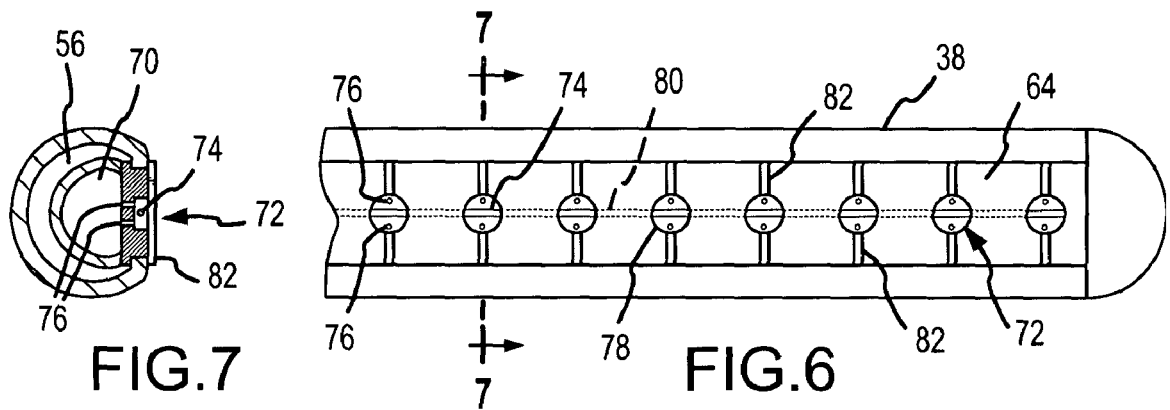
FIG. 6 is a partial side view of the catheter shown in FIG. 5.
FIG. 7 is a section view of the catheter taken along line 7-7 of FIG. 6.
Figure 8:
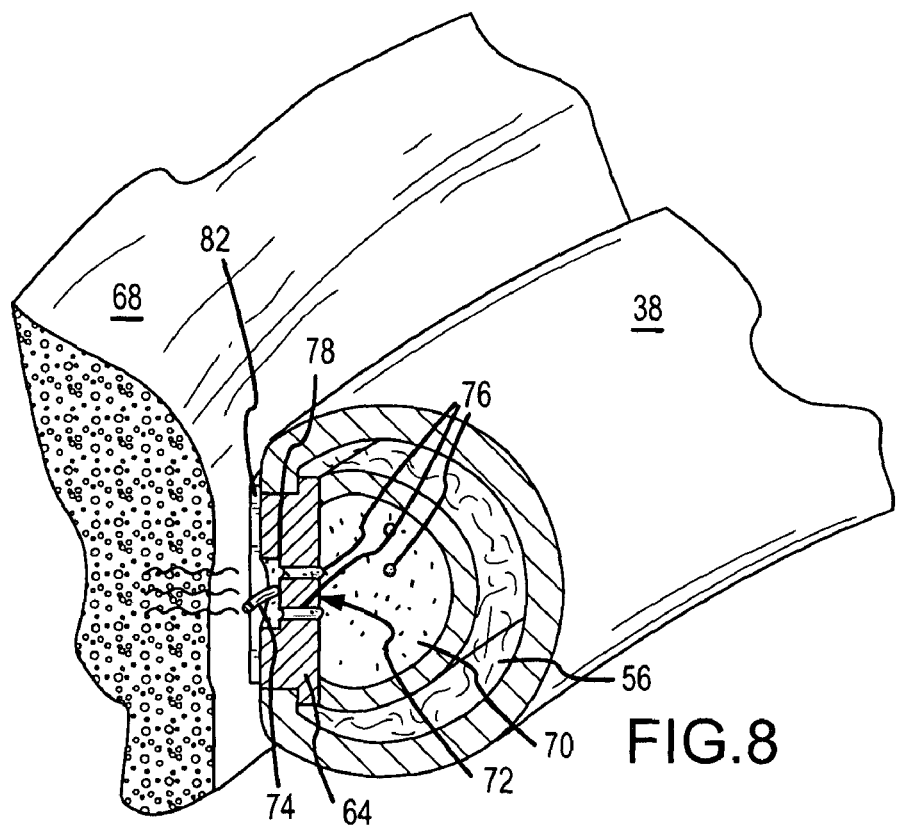
FIG. 8 is a partial isometric view of the catheter of FIG. 5 located in partial or complete contact with a target tissue.

FIGS. 3A-3C illustrate an isometric view, a top view, and a side view, respectively, of one particular implementation of a shapable ablation catheter 38, in accordance with the present invention. The catheter shown in FIGS. 3A-3C includes a precurved loop shape 54 at the distal end region of the catheter. The loop is particularly suited for performing an ablation procedure at a pulmonary vein in the left atrium. The catheter shown in FIGS. 3A-3C also shows the precurved loop shape of the distal region of the catheter in a relaxed contracted state before introduction of a fluid into an actuating lumen 56 (the actuating lumen is shown in FIGS. 5, 7, 8, and others). FIGS. 4A-4C illustrate the ablation catheter 38 of FIGS. 3A-3C with fluid under pressure introduced into the actuating lumen to deflect the precurved catheter shape into a larger partial loop. Referring to both FIGS. 3A-3C and FIGS. 4A-4C, the shapable ablation catheter includes the shaft or tubular body 50 and the ablation region 42. The ablation region is positioned generally along the curve 54 at the distal end region of the ablation catheter. The ablation region may be from 1 to 30 millimeters in length, in some embodiments. As will be discussed in further detail below, the ablation region may include one or more manifolds, ablating electrodes, a combination thereof, or some other structure or arrangement suitable for use in conveying ablation energy to a target tissue. Hereafter, the term "ablation energy" will be used to refer to any energy type used to ablate tissue, such as radio frequency (RF), direct current, alternating current, microwave, ultrasound, and ohmic.

Some embodiments of the ablation catheter also contain one or a plurality of radiopaque tip marker bands (not shown) near the distal end and/or along the length of the catheter. The radiopaque tip markers allow the physician to track the location of the ablation catheter traveling within the body through radiopacity. The tip markers may also be located at the distal end and/or along the length of the sheath 40.

As with the sheath 40, the tubular body 50 of the ablation catheter 38 is a flexible and resilient tubular structure. In the examples shown in the various figures herein, the tubular body defines a precurved loop-shape portion 54, part of which includes the ablation region 42. The loop-shape of the tubular body and the ablation region therein facilitates formation of a continuous or nearly continuous lesion around the inside wall within one or more of the pulmonary veins or within the left atrium at the ostium to one or more of the pulmonary veins when ablation energy is transmitted to the target vein.

To properly orient and shape the loop 54, the distal region of the catheter 38 defines a first generally straight region 58 that is generally coaxially aligned with the distal end region of the sheath 40. Following the generally straight region is a multidimensional curved region 60 of the catheter including a positioning curve 62 and the loop-shape curve 54. The curved regions of the distal end region of the ablation catheter may be fabricated with a bonded polymer. As best illustrated in FIGS. 3C and 4C, the positioning curve region 62 is adapted to position the loop region 54 so that the plane defined by the loop is roughly perpendicular to the longitudinal axis of the distal end region of the sheath 40 and/or shaft 50. The loop region 54 is shown in the figures as defining a generally circular-like, unclosed loop shape. The loop region, however, may form any closed or unclosed curved or generally arcuate shape, such as a partial or complete circle or ellipse.

In some embodiments of the ablation catheter a shaping element 64 is employed to provide the precurved shape of the distal end region of the catheter as shown in FIGS. 3A-3C. The shaping element may be fabricated of a super elastic metal alloy material, such as a nickel-titanium alloy. One such suitable nickel-titanium alloy is commonly referred to as "Nitinol." Generally, a suitable super elastic material for the shaping element is a shape memory alloy with a transformation temperature below that of the human body temperature. Alternatively, the shape memory alloy may also have a transformation temperature above that of the human body. In this alternative utilization, an electric current is applied to the shape memory alloy material to convert it into a super elastic state. When such a super elastic shape memory alloy is utilized, the shaping element 64 may be precurved and it will retain its curvature to cause the ablation catheter to form the loop when the catheter is moved out of the sheath, while still retaining sufficient flexibility to support the ablation catheter as it is pressed against the target tissue.

As shown in FIGS. 3A-C and 4A-C, a distal tip 66 is secured to the distal end of the catheter 38. The tip seals the end of the actuating lumen 56 (see also FIG. 5 and others). The distal tip may define a blunt end, may include an electrode configured to energize and ablate tissue, may be a sensing electrode to provide a mapping function, or may include other functionality. In the event the tip includes an electrode or sensor, it will include a wire or wires strung through the catheter to the connector 44 at the proximal end region of the catheter.

All or a portion of the loop-shaped region 54 of the catheter includes the ablation region 42. In one implementation, the ablation region is arranged generally along the outer portion of the curve 54. Regardless of how the loop and the overall curved shape of the catheter is obtained, the overall curved shape of the catheter is defined so that when the loop portion is directed toward one of the pulmonary veins a portion of the ablation region 42 is placed in partial or complete circumferential contact with a wall of the target vein. When positioned as such, ablating elements located at the ablation region may be energized to form a complete or nearly complete circumferential lesion adjacent to or within the pulmonary vein. Various ablating elements and arrangements are discussed below. Such a circumferential lesion can partially or completely eliminate harmful signals from traveling through one of the pulmonary veins into the heart.

FIGS. 5-8 illustrate in further detail the embodiment of a shapable ablation catheter 38 illustrated in FIGS. 3A-4C. Particularly, FIG. 5 is a partial top view of the ablation catheter, FIG. 6 is a partial side view of the ablation catheter, and FIG. 7 is a section view taken along line 7-7 of FIG. 6. Finally, FIG. 8 is a conceptual partial isometric section view of the shapable ablation catheter during performance of an ablation procedure on a section of target tissue 68.

As best shown in FIGS. 5, 7, and 8, the ablation catheter 38 includes the steering or actuating lumen 56 and a second inner lumen 70. The inner lumen or ablating fluid lumen 70 provides a flow path for saline or another ablating fluid to flow along the tubular body of the catheter to a plurality of manifolds 72 arranged along the ablation region 42 of the catheter. When the fluid reaches the manifold, it flows through the manifolds and out of the catheter body. As the fluid flows through the manifolds, it encounters an energized electrode 74 which heats the fluid within the manifold. The heated fluid flows out of the manifold and against a target tissue to ablate the tissue. Moreover, the fluid also provides a conduction path for the ablation energy to the target tissue to ablate the target tissue.

Figure 22:
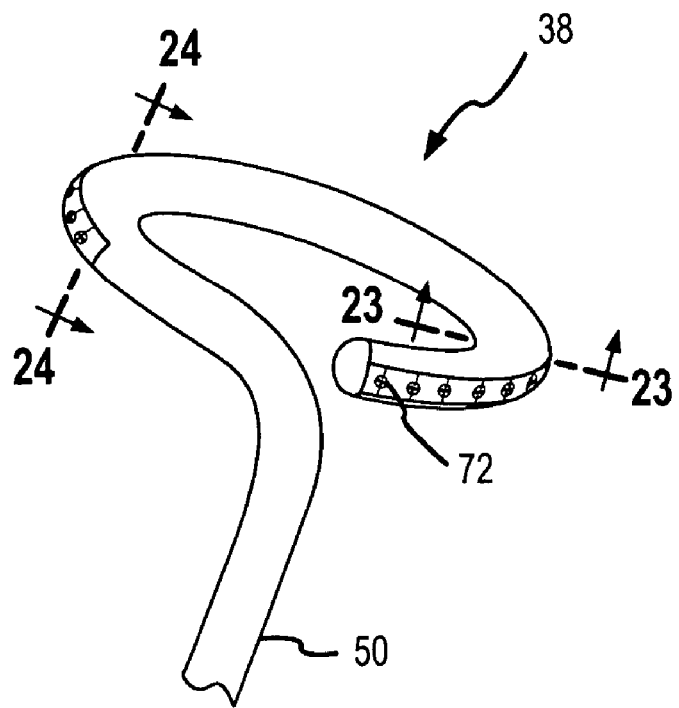
FIG. 22 is an isometric view of an ablation catheter employing a plurality of ablation fluid manifold arrangements for directing ablation fluid to a target tissue, in accordance with one embodiment of the present invention.
Figure 23:
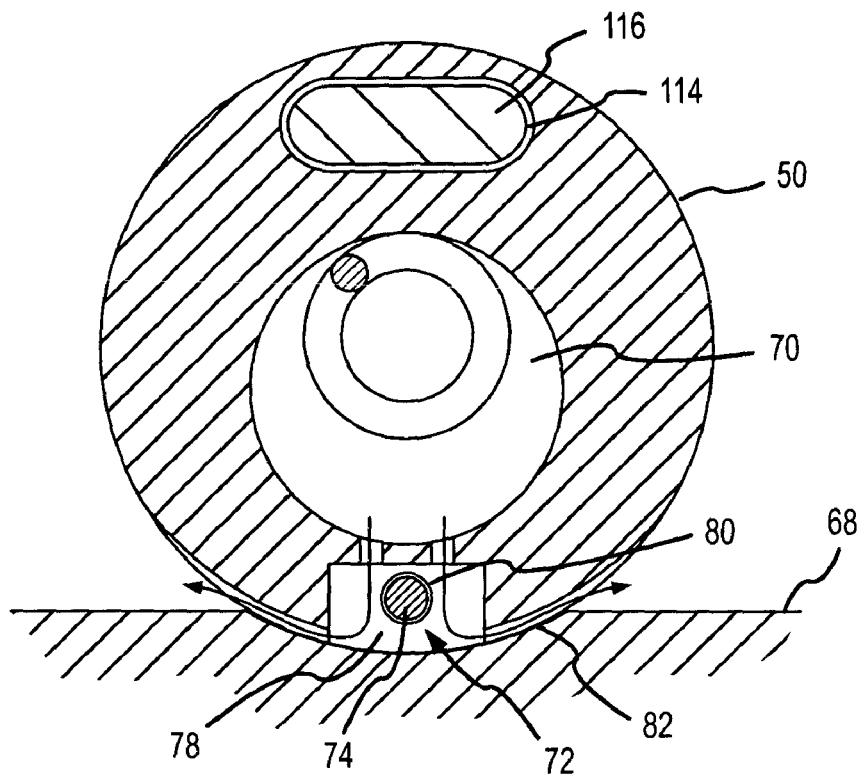
FIG. 23 is a section view taken along line 23-23 of FIG. 22.
Figure 24:
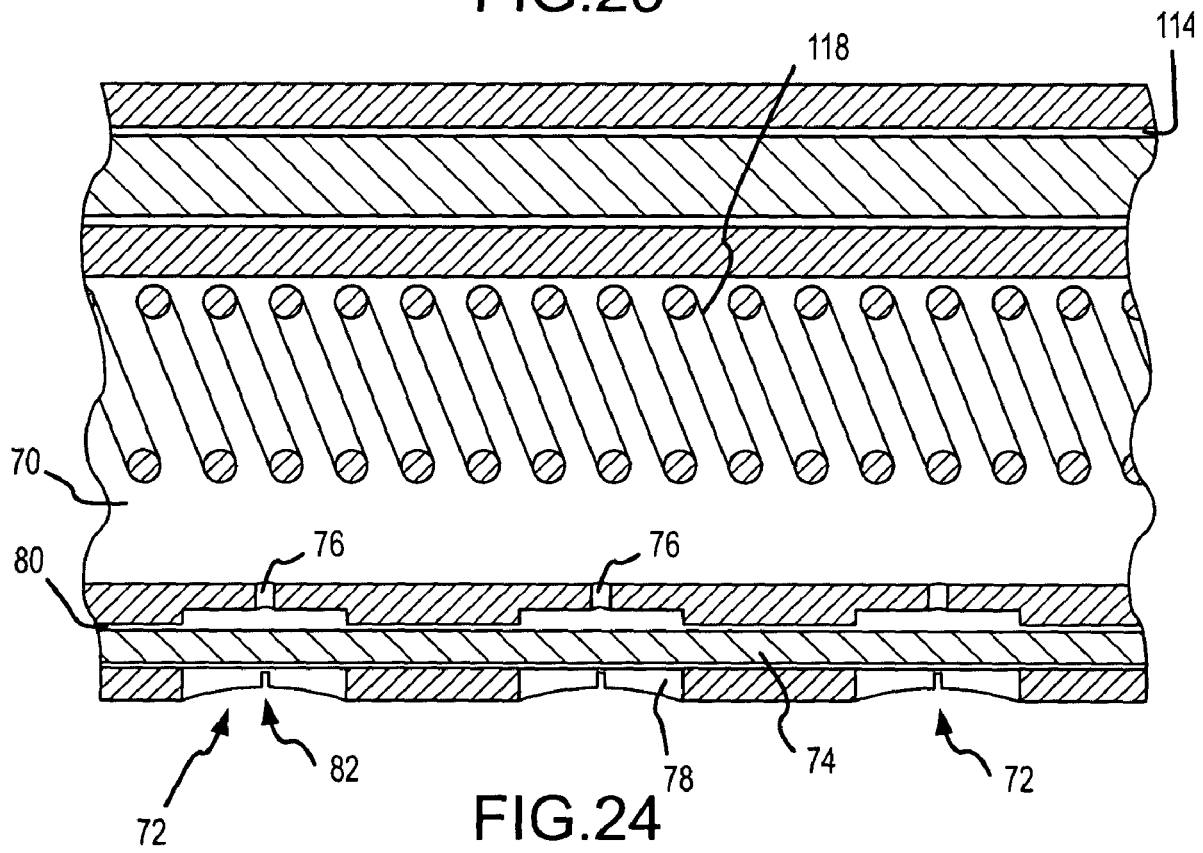
FIG. 24 is a section view taken along line 24-24 of FIG. 22.

One example of an ablation catheter manifold conforming to aspects of the present invention is shown in FIGS. 5-11. An alternative example of an ablation catheter manifold conforming to aspects of the present invention is shown in FIGS. 22-24. Referring now to FIGS. 5-11, some implementations of an ablation catheter include several manifolds 72 along the ablation region 42. The manifolds may be formed in the shaping element 64, in one example. The manifolds may also be formed in the tubular side wall of the catheter or otherwise provided. Each manifold 72 includes at least one manifold inlet port 76 in fluid communication with a larger ablating fluid outlet port 78. As such, fluid from the inner lumen 70 may pass through the smaller inlet port(s) into the larger ablating fluid port. In one particular implementation of the catheter, the inner lumen defines about a 0.05 inch diameter, the manifold inlet port(s) defines about a 0.002 inch diameter, and the ablating fluid outlet ports define about a 0.020 to 0.025 inch diameter.

The arrangement of the manifolds 72 and their location along the length of the ablation region 42 isolates each ablating fluid outlet port 78 from the adjacent outlet port or ports. Isolation of the ablating fluid outlet ports helps to evenly distribute saline or another ablating fluid amongst all or most of the ablation fluid ports despite uneven contact or contact pressure of the ablation region against target tissue. Isolation of the ablation fluid ports also helps to inhibit non-uniform dynamic blood pressure within the heart or a vessel from being communicated from one ablation port to another while the catheter is being introduced and manipulated within the heart or a vessel.

As mentioned above, the ablating fluid is energized and heated by contacting the electrode 74, and the fluid conveys ablation energy to the tissue. In the catheter of FIGS. 5-11, the electrode is arranged within an electrode lumen 80 that is formed in the shaping element 64. The electrode lumen is arranged generally parallel with the longitudinal axis of the catheter. The electrode lumen is further arranged so that the electrode runs through the ablating fluid outlet port 78 of each manifold 72. In operation, saline or other fluid flows through each manifold inlet port 76 and into the larger outlet port 78. In the transition area where the manifold inlet ports are in fluid communication with the outlet port, the fluid encounters the electrode 74. As the fluid flows around the charged electrode and toward the target tissue, the ablation energy from the energized electrode is conveyed via the ablation fluid to the target tissue. The target tissue is thereby primarily heated and ablated through ohmic heating. The ablation region is generally configured so that the electrode does not come in direct contact with the target tissue. However, in some instances such direct contact may occur in which case ablation energy, such as radio frequency energy, passes from the electrode directly into the target tissue and thereby provides an additional way to ablate tissue.

The manifold 72 shown in FIGS. 5-11 is illustrated with two manifold inlet ports 76. However, embodiments conforming to the present invention may include any number of manifold inlet ports, such as from between one and six manifold ports. Having two or more manifold inlet ports helps to reduce the likelihood of saline stagnation areas within the outlet port 78. If saline stagnates within the outlet port, it may experience excessive heating from prolonged contact with the electrode. The angle of entry into the outlet port and arrangement of the manifold inlet ports 76 may be varied to provide saline circulation, such as a vortex, within the outlet port and flowing outwardly toward the target tissue. Such a swirling vortex motion may help to more uniformly energize and heat the saline for the ablation procedure.

After the ablation region 42 of the catheter is properly positioned adjacent or in close proximity to the target tissue, ablating fluid is introduced into the ablation fluid lumen 70 via a valve 52 along the proximal end region of the catheter. The ablating fluid flows within the lumen along the length of the catheter and then flows into the loop-shaped ablation region 42 of the catheter where the ablation procedure is performed. In some particular implementations, the ablation region may be anywhere from about one centimeter to about ten centimeters in length along the distal portion of the catheter. In various embodiments, there may be numerous ablation manifolds 72 arranged along the outer curve of the loop. As mentioned earlier, in some procedures it is desirable to provide a generally continuous and circumferential ablation around the ostium to a pulmonary vein or within a pulmonary vein. As such, ablation fluid should be distributed fairly evenly to each ablating fluid outlet port 78 along the ablation region. The manifold arrangement along the ablation region helps to more evenly distribute fluid along the curves in the inner lumen 70 along the ablation region. Particularly, by using one or a plurality of smaller manifold inlet ports 76 flowing into a larger ablation fluid outlet port 78, fluid is more readily distributed along the curve of the inner lumen.

As shown best in FIGS. 5-11, in one particular implementation, each manifold includes channels 82 or slots extending away from each ablation fluid port. When the ablation catheter is pressed against a target tissue, the channels provide a path into the bloodstream for the saline flowing out of the ablation fluid outlet port 78. Without a channel or some other exit path for the saline, the saline may be more readily blocked by the tissue and will not as readily flow through the manifold and across the electrode 74 in order to conduct ablation energy and fluid to the target tissue. In one example, the channel is arranged such that some portion of at least one of the channels will extend away from the target tissue in order to provide at least one exit path for the saline flowing through the manifold.

Generally, the channels 82 may be sized to provide little resistance to saline flow, and optimize the diversion of ablation energy, e.g., electrical current, from the target tissue. In one such channel configuration, the depth of the channel is about 0.005 inch and the width is about 0.003 inch. In this configuration, the depth of the channel is larger than the width, which helps to stop tissue from deforming into the channel and occluding the channel and manifold when the ablation region 42 is pressed into or situated against target tissue.

As mentioned above, a catheter in accordance with one example of the present invention includes or defines an actuating lumen 56. Unlike the inner lumen 70, which has one or more manifolds 72 for saline to flow out of the lumen to ablate tissue, the actuating lumen 56 only includes an inlet port or ports in fluid communication with a valve or valves at or near the proximal end region of the catheter to allow saline or some other fluid to flow into the actuating lumen. Otherwise, the actuating lumen is sealed so that the actuating fluid does not flow out of the distal region of the catheter.

As mentioned above, the shaping element 64 may include a predefined shape, such as a curve. In the configuration of FIGS. 5-8, the actuating lumen extends to the distal end of the catheter and is configured to work with the curved shaping element. Particularly, the actuating lumen 56 is arranged so that it is offset from the shaping element 64. As such, fluid introduced into the actuating lumen flows along the length of the lumen until it reaches the end cap or some other element impeding its flow. When the fluid flows against the end cap, pressure builds within the actuating lumen. Fluid pressure within the actuating lumen offset from the shaping element creates a bending moment and causes the curved shaping element to begin to straighten.

As discussed herein, the curve of the catheter shaft may be present in the shaft itself rather than in a shaping element. Moreover, the catheter may not be precurved. In addition, the actuating lumen may extend to the distal end of the catheter, or it may terminate at other points along the length of the shaft. Moreover, a plurality of actuating lumens may be employed in various configurations to steer a catheter to any target tissue.

In one implementation, the shaping element 64 is preset in a loop and the ablation region 42 of the catheter takes on the loop shape 54. Referring again to FIGS. 3A-3C, the curved shape of an ablation catheter 38 in the unactuated position is shown. Referring again to FIGS. 4A-4C, the curved shape of an ablation catheter in the actuated position is shown. When the ablation catheter is first pressed outwardly from the sheath 40, it takes the shape as shown in FIGS. 3A-3C. This curved shape may also be preset or precurved in the tubular body of the ablation catheter. By introducing fluid into the actuating lumen, the loop portion of the ablation catheter expands outwardly, such as is shown in FIGS. 4A-4C. By removing fluid from the actuating lumen, the loop may contract or reduce in size to some extent. By removing all actuating fluid or at least enough actuating fluid to cause the pressure in the actuating lumen to become less than the pressure required to straighten or bend the ablation catheter, the ablation catheter will return to the shape as shown in FIGS. 3A-3C.

Referring now to FIGS. 9-11, a top view, a side view, and a section view, respectively, of an alternative ablation catheter 38 is shown. The ablation catheter is shown in an uncurved form; however, the ablation catheter may be precurved in some particular implementations. The catheter of FIGS. 9-11 does not include an actuating lumen separate from the inner lumen as with the catheter of FIGS. 5-8. Instead, the catheter includes, defines, or is integral with a single fluid lumen 84. A shaping element 64 is connected with the catheter. Along the ablation region of the catheter, the shaping element defines a plurality of manifolds as described with respect to the catheter of FIGS. 5-8.

The shaping element 64 may be precurved so that the ablation region 42 of the catheter will take on a shape similar to that of the catheter of FIGS. 3A-3C when the catheter is moved out of the sheath. In order to change the shape of the ablation region of the catheter after it is pressed out of the sheath, fluid is introduced into the single fluid lumen 84. The fluid fills the lumen and causes pressure to build within the lumen 84 which in turn causes a bending moment against the precurved shaping element 64. Unlike the embodiment including a separate actuating lumen, the fluid lumen of the embodiment of FIGS. 9-11 also carries saline or some other conductive fluid medium to the manifolds 72. The fluid flows through the manifolds to become energized and subsequently convey ablation energy to the target tissue. The shaping element of the catheter of FIGS. 9-11 also defines an electrode lumen 80 housing an electrode 74 similar to the electrode lumen and electrode of FIGS. 5-8. In the catheter implementation of FIGS. 9-11, fluid flow into the fluid lumen 84 and through the manifolds must be regulated in order to maintain the appropriate amount of fluid flow to ablate the tissue and also to deflect the catheter the appropriate amount so that the ablation region is located adjacent the target tissue as fluid flows out the ablating outlet ports 89.

One or more sensors 86, such as temperature sensors, electrophysiological signal sensors, or other sensors, are placed along the length of the ablation region. The temperature sensors are used to monitor the temperature in the region of the tissue being ablated in order to determine if the appropriate temperature is being achieved for ablation. For electrophysiological sensors, a first sensor, in one example, may transmit a signal, and one or more additional sensors, preferably arranged on the opposite side of the manifolds, electrodes, or other ablation sources, may be configured to receive the signal. Depending on the time taken to receive the signal, it can be determined whether an adequate lesion was formed.

In one particular arrangement, the sensors 80 define a sensing section 88 and leads 90 extending from each end thereof. The sensing section is arranged generally parallel to the longitudinal axis of the catheter. The leads extend into the lumen 84 through apertures defined in the shaping element. Wires (not shown) may be strung to the leads along the lumen and connected with the connector 44 at the proximal end of the catheter. In the catheter of FIGS. 9-11, sensors are arranged on either side of the manifold so that the sensing sections extend generally between adjacent channels. Sensors may be employed in various catheter arrangements conforming to the present invention.

Figure 12:
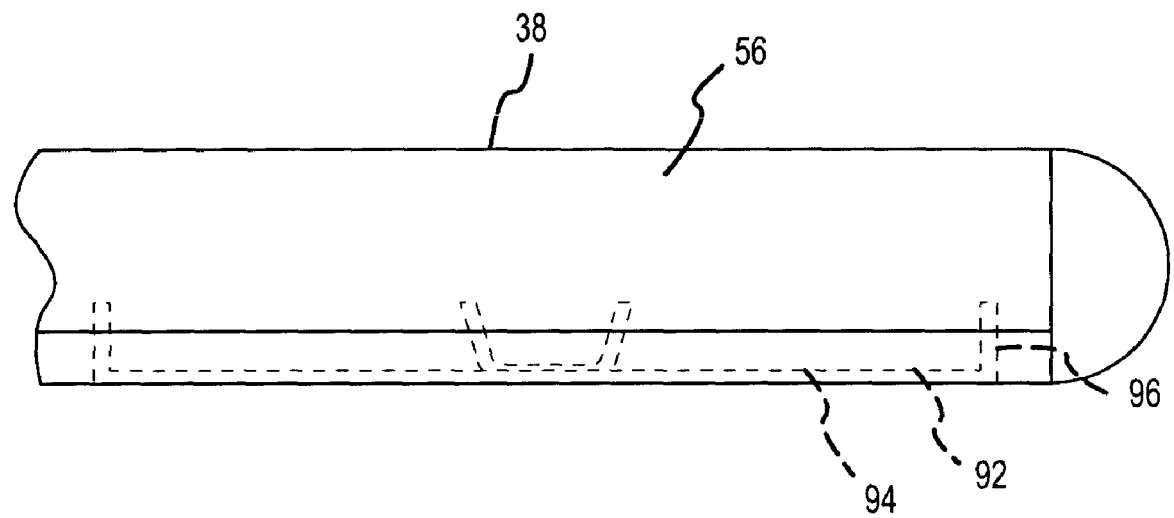
FIG. 12 is a partial top view of a distal portion of a shapable catheter, in accordance with one embodiment of the present invention.
Figure 14:
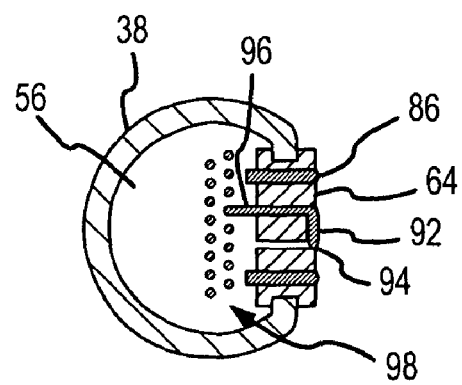
FIG. 14 is a section view of the catheter taken along line 14-14 of FIG. 13.
Figure 13:
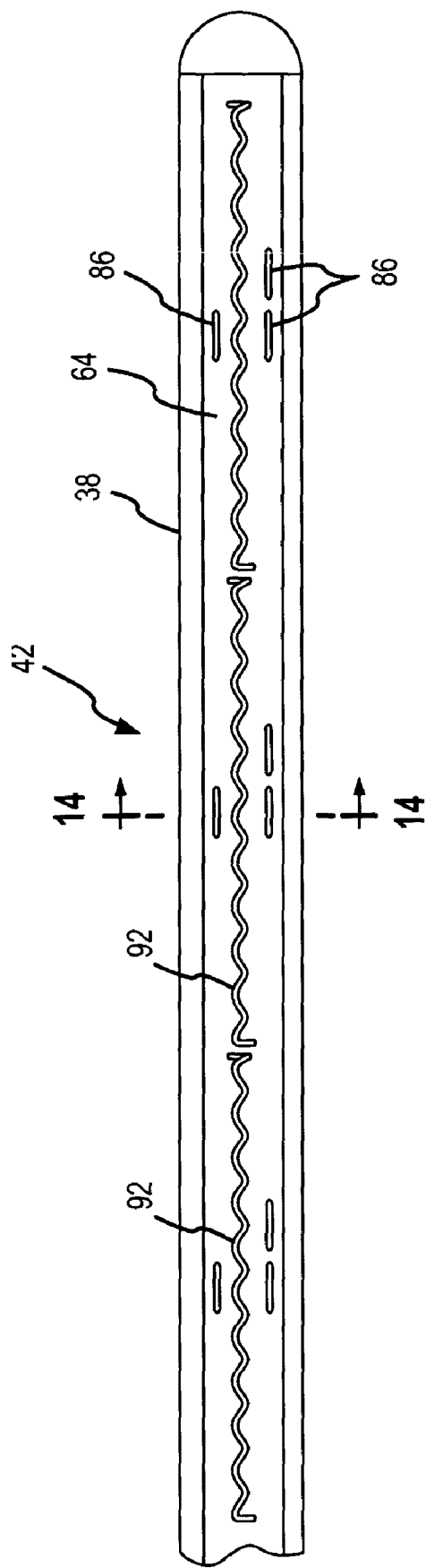
FIG. 13 is a partial top view of the catheter of FIG. 12.

FIGS. 12-14 illustrate an alternative catheter 38 conforming to aspects of the present invention. Particularly, FIG. 12 is a partial top view of a second alternative ablation catheter. FIG. 13 is a side view of the ablation catheter shown in FIG. 12, and FIG. 14 is a section view taken along line 14-14 of FIG. 13. The ablation catheter is shown without a precurved loop. However, the catheter of FIGS. 12-14 may be configured with a precurved loop portion at the ablation region, or include structure to facilitate formation of a loop. In either a curved or uncurved configuration, the catheter may define or include an actuating lumen 56. The actuating lumen, similar to the actuating lumen of the catheter of FIGS. 3-8, has at least one inlet port (not shown) at the proximal end region of the catheter. The inlet port is connected with a valve 52 to control the volume and/or pressure of fluid within the lumen. In this example, the distal end of the actuating lumen is sealed with an end cap 66. Alternatively, an electrode, sensor or other device may be located at the distal end of the catheter. Nonetheless, the actuating lumen, in this embodiment, is sealed except for the inlet port or ports to allow the inlet of actuating fluid.

Further, the catheter may include a shaping element 64 with or without a preset curvature, which may be the same or similar to the curvature of the catheter illustrated with respect to FIGS. 3A-3C. As with other embodiments discussed herein, the center of the actuating lumen 56 is offset from the shaping element 64. As such, when fluid under pressure is introduced into the actuating lumen it causes a bending moment to deflect the shaping element and thereby change the shape of the catheter.

The catheter of FIGS. 12-14 includes at least one elastic electrode 92 defining a saw tooth pattern. The elastic electrode is oriented generally longitudinally along at least a portion of the length of the ablation region 42 of the catheter. In some catheter implementations, such as is shown in FIGS. 12-14, a plurality of elastic ablation electrodes 92 are employed along the length of the ablation region of the ablation catheter. Unlike the catheter embodiments of FIGS. 3A-11, the ablation catheter of FIGS. 12-14 does not include one or more manifolds for directing energized saline to the target tissue. Instead, ablation occurs by orienting the elastic electrode in contact with target tissue and energizing the electrode. The electrode then carries ablation energy directly to the target tissue. The electrode includes an ablation section 94 with leads 96 extending from each end thereto. The leads extend into the lumen 56 through apertures in the shaping element. Wires 98 are connected to each lead and are strung within the lumen along the length of the catheter to the connector. The catheter may also include one or more sensors 86 arranged similarly to that of FIGS. 9-11.

Defining a saw tooth pattern and being fabricated of a resilient and elastic material, the electrode 92 conforms to changes in the shape of the ablation region. For example, if the ablation region defines a loop, when the loop is expanded, the saw tooth pattern of the electrode allows the electrode to expand or lengthen to conform with the expansion of the loop. Conversely, if the loop is contracted, the saw tooth pattern of the electrode allows it to compress to conform with the tightening or contraction of the loop. The electrode may be fabricated from various materials, combinations of materials, alloys, and the like, such as platinum, gold, stainless steel, gold-plated stainless steel, and a composite of conductive polymer metal.

The elastic electrode 92 is also configured to either assist in deflecting the catheter outward from its initial precurved condition, or to resist the force imparted by the fluid in the lumen 56 and/or assist in returning the catheter to its initial preactuation shape. As is known in the art, a spring or other elastic element will regain its original shape after being compressed or extended. In an embodiment of the present invention employing an elastic electrode, the electrode may be connected with the catheter such that it is either compressed or extended when the loop portion of the catheter is in its relaxed state. If the electrode is compressed, then it will assist the shaping element 64 in causing the catheter 38 to form a curved shape. If the spring-loaded electrode 92 is in the extended position, then it will resist the curving force introduced by the shaping element.

FIGS. 15A-18 illustrates two configurations of a catheter 38 employing an actuating lumen 56 or a plurality of actuating lumens arranged to terminate along various points along the length of the shaft 50 of the catheter. As with other embodiments, each actuating lumen includes an inlet port (not shown) arranged along the proximal region of the lumen. The inlet port is in fluid communication with a valve 52 to control the flow of fluid into the lumen. Otherwise, the actuating lumens are sealed.

More particularly, FIGS. 15A,B and 16 illustrate side views, and a section view, respectively, of one example of a catheter 38 including an actuating lumen 56 terminating at some point along the length of the shaft 50. The actuating lumen may terminate at any point between the proximal and distal end of the shaft. In the example of FIGS. 15A-16, the catheter is not precurved. FIG. 15B illustrates the catheter of FIG. 15A when fluid is within the actuating lumen. When fluid is introduced into the actuating lumen and the fluid flow is impeded by the terminal distal end of the actuating lumen, a bending force is imparted by the fluid on the shaft. As such, the shaft will bend to some degree along the force line of the bending force.

FIGS. 17A,B and 18 illustrated side views, and a section view, respectively, of one example of a catheter 38 including a plurality of actuating lumens 56, in this example four actuating lumens, terminating at some point along the length of the shaft 50. The actuating lumens may terminate at any point between the proximal and distal end of the shaft. Moreover, any of the actuating lumens (whether arranged alone or in multiple actuating lumen arrangements) may be arranged anywhere along the circumference of the tubular body shaft. In some implementations, the force imparted by the fluid in the actuating lumen is along a line between the longitudinal axis of the actuating lumen 56 and the longitudinal axis of the catheter shaft 50. For example, FIG. 17B illustrates the catheter of FIG. 17A with fluid introduced into the lower actuating lumen. Here the force is along the line between the lower lumen and the longitudinal axis of the shaft; as such, the catheter is bent upward by the force of the fluid in the lumen.

In a catheter employing a plurality of actuating lumens 56, each lumen may be arranged to terminate at different points along the length of the catheter. In such arrangements, the catheter may be steered or its shape changed at multiple areas along its length. In a catheter employing a plurality of actuating lumens, each lumen may also be arranged to terminate at the same point along the length of the catheter. In such an arrangement, fluid may be introduced into one or more of the lumens and the force of the fluid monitored to bend the shaft in any plane defining 360 degrees around the catheter. As such, the catheter may be bent or steered in any direction.

Figure 20:
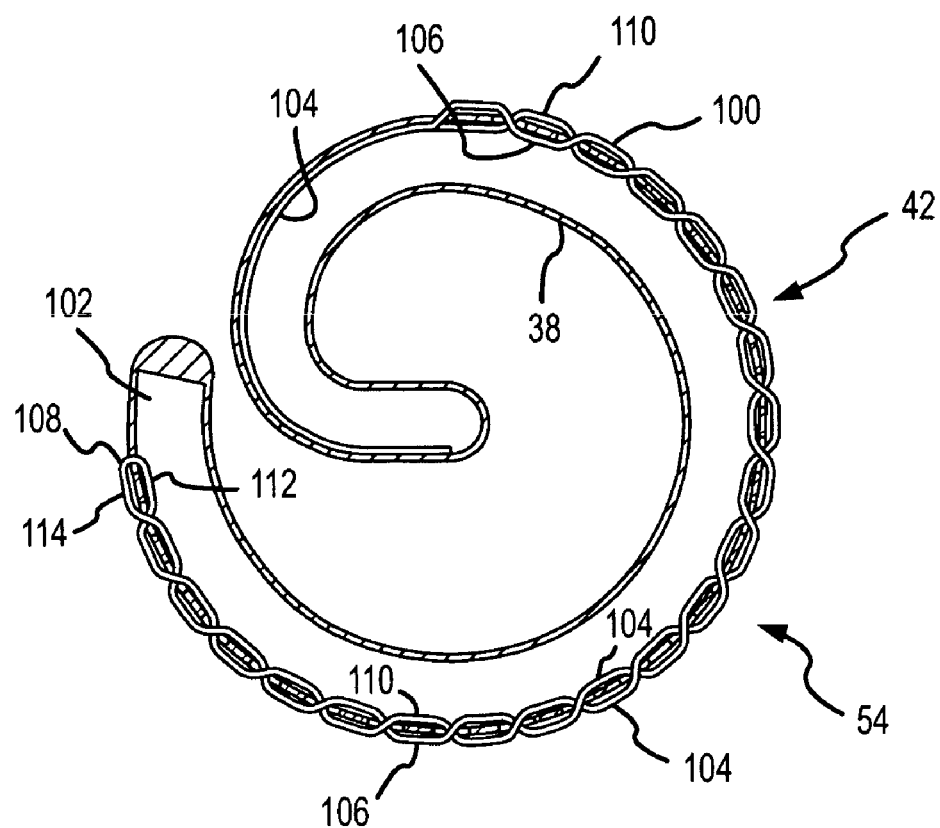
FIG. 20 is a section view taken along line 20-20 of FIG. 19.
Figure 19:
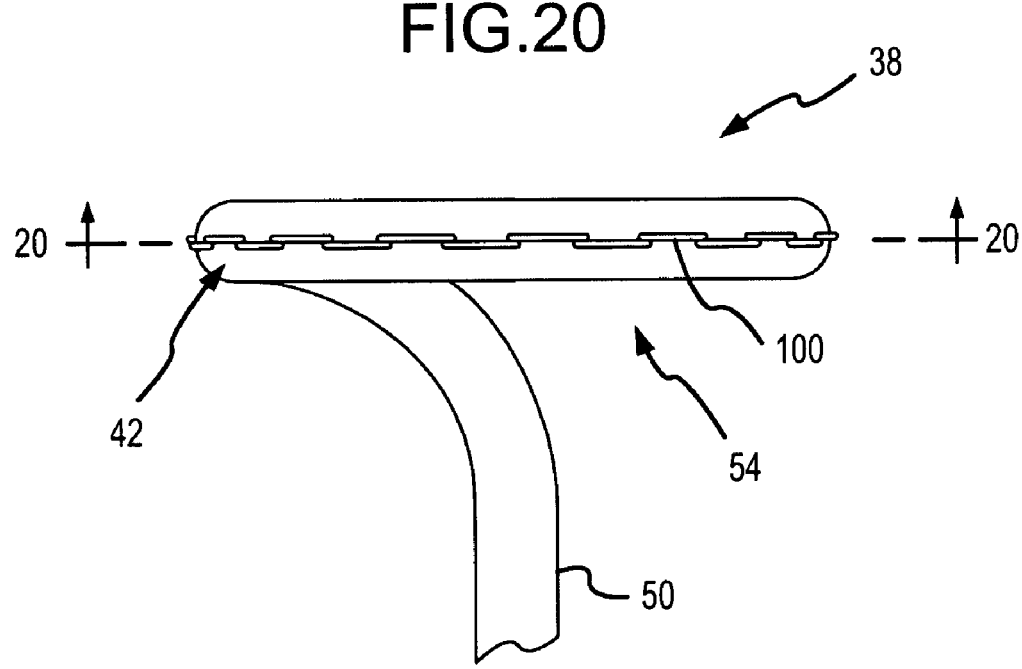
FIG. 19 is a side view of the distal end region of a precurved catheter employing an interlaced electrode in accordance with one embodiment of the present invention.

FIGS. 19 and 20 illustrate a catheter 38 employing an interlaced or interwoven electrode strand 100 situated around the outside curve of the ablation region 42 a catheter configured with a loop 54 at the distal end. Particularly, FIG. 19 is a side view of the distal end region of the catheter, and FIG. 20 is a section view taken along line 19-19 of FIG. 19. An interlaced electrode arrangement, such as is illustrated in FIGS. 19-20, may be employed in any type of ablation catheter arrangement, such as a conventional ablation catheter arrangements or any of the ablation catheter arrangements conforming to various aspects of the present invention and discussed herein. Both the elastic electrode arrangement 92 of the ablation catheter of FIGS. 12-14 and the interlaced electrode arrangement 100 of the ablation catheter of FIGS. 19 and 20 may be employed to provide a continuous or nearly continuous lesion at a target tissue (e.g., a circumferential lesion at or around the inner wall of a pulmonary vein). Moreover, the electrode arrangements of FIGS. 12-14 and 19-20 help to isolate ablation energy being directed to the target tissue from the blood around the target tissue.

Referring to FIG. 20, the interlaced electrode arrangement 100 includes, in one particular configuration, a single electrode strand 104. The electrode strand is connected at its proximal end (not shown) to an ablation energy source. The distal end region of the strand is interlaced or interwoven along the outer curve of the loop-shaped ablation region of the catheter. It may, however, be interwoven along other areas of the ablation region, e.g., the inner part of the curve, the top of the curve, etc. Still referring to FIG. 20, at the top of the view it can be seen that the electrode strand is strung to the ablation region through a lumen 102 running along the length of the catheter. The tubular body of the catheter includes at least one lumen, but may include additional lumens to house, for example, steering or actuating fluid, a guide wire, a shaping element, and the like.

Along the distal end region of the looped-shape ablation region 42 of the catheter, the electrode strand 104 defines a first interlaced section 106 running toward a U-shaped section 108 of strand near the distal end of the catheter. The strand further defines a second interlaced region 110 running away from the U-shaped section of strand. The first interlaced section of strand defines a plurality of strand sections that are alternatingly arranged outside the lumen 102 and within the lumen 102. Near or at the distal end of the catheter, the electrode strand defines an end strand section 112 located within the lumen followed by the U-shaped strand section 108. The U-shaped section defines a convex strand section oriented toward the distal end of the catheter. Along the convex section of the electrode strand, the electrode strand emerges from within the lumen and defines a second end section 114 located outside the catheter. Following the second end section, the electrode strand defines the second interlaced region 110 running along the loop portion of the catheter toward the proximal end of the catheter.

The second interlaced region 110 also defines a plurality of strand sections that are alternatingly arranged outside the catheter and within the lumen. The strand sections of the first interlaced region 106 and the second interlaced region 110 are arranged along the outside of the catheter to work in concert to define a generally continuous section of exposed electrode. As such, the strand is interlaced so that exposed strand sections of the first interlaced section are located adjacent exposed strand sections of the second interlaced section. Having a continuous or nearly continuous exposed electrode along the outer circumference of the loop allows the interleaved electrode strand arrangement to ablate a continuous or nearly continuous lesion along a section of target tissue. Moreover, being interlaced, the electrode weave may conform to change in the curve shape of the catheter.

Figure 21:
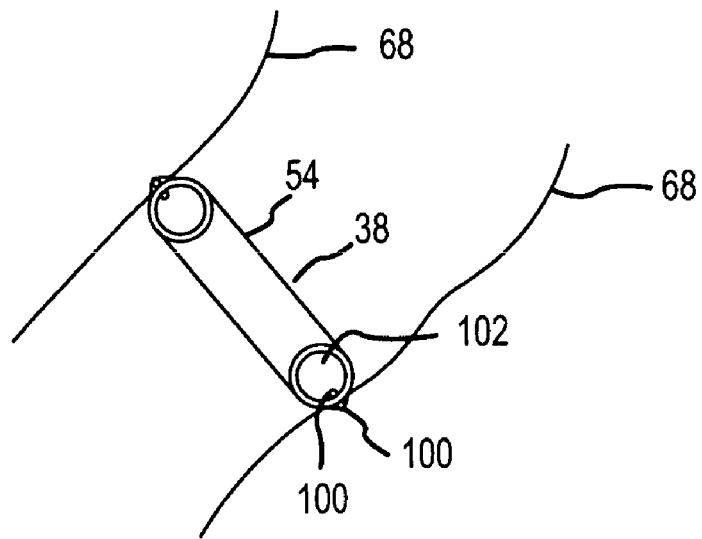
FIG. 21 is a section view of the catheter of FIG. 19 when inserted into a vein to form a circumferential lesion therein.

As shown best in FIG. 19, the exposed sections of interlaced strand are longitudinally arranged along the outside circumference of the loop. The total width of the electrode ranges from one strand width (i.e., the diameter of a strand) to two strand widths where the adjacent strand sections overlap. Moreover, as shown best in FIG. 13, the saw tooth pattern of the elastic electrode 92 also defines a fairly narrow longitudinally arranged electrode. FIG. 21 is a partial side section view of the catheter of FIGS. 19 and 20 being used in an ablation procedure in one of the pulmonary veins. When the loop portion 54 of the catheter 38 is expanded outwardly, similar to, for example, the loop as shown in FIGS. 4A-4C, the outer portion of the loop will be pressed against the target tissue 68. Defining a narrow electrode width, both the interlaced electrode arrangement of FIGS. 20-21 and the elastic electrode arrangement of FIGS. 12-14 will be pressed into the target tissue leaving little or no section of the electrode strand exposed to blood in the vicinity of the electrode and target tissue. This helps to concentrate ablation energy at the target tissue and avoid ablation energy transfer to the blood around the target tissue.

The tubular body or shaft 50 of the catheter 38 may be fabricated to define a plurality of apertures along the outside circumference of the catheter through which the electrode strand is interlaced. The apertures may be undersized so that when the strand is threaded through the apertures a seal or partial seal is formed to help avoid having body fluid enter into the lumen 102 through the apertures. Saline may also be input into the lumen to flush blood and other body fluids out of the apertures. The saline may also be used to flush body fluid away from the electrode strand so that body fluid does not stagnate around the electrode. It is possible to employ a plurality of interlaced strands arranged sequentially, arranged parallel, or in other configurations, and such strands may be separately energized.

Conventional ablation energy sources provide a limited amount of ablation energy to the electrode. As such, it is important to focus that energy on tissue ablation, and avoid having that energy be diverted into the bloodstream, which blood typically has a lower resistance than tissue and thus provides a lower resistance path for the energy. The elastic electrode and the interlaced electrode both focus the ablation energy to the tissue by providing a mechanism whereby the electrode is exposed primarily to the target tissue, and little or none of the electrode is exposed to the blood when the electrode is energized. Moreover, by providing a continuous or nearly continuous electrode surface, the elastic electrode 92 and the interlaced electrode 100 allow the physician to ablate a continuous lesion in or at the target vein with little or no adjustment of the catheter at the target tissue once the catheter is properly oriented at the start of the procedure. In comparison, for example, using a conventional ablation catheter employing an electrode at the tip of the catheter, a physician must move the catheter numerous times to locate the tip along various points of an arc within the vein. At each point, the physician creates a small lesion with the tip, and then must move the tip to the next point to create a lesion around the vein.

For purposes of stopping stray electrical signals from flowing into the left ventricle via the pulmonary veins, it is sufficient to have a one cell length ablation in the path of the stray signal to block that signal. As such, the strand width of either the elastic electrode 92 or the interlaced or woven electrode 100 is adequate to ablate at least one cell and likely much more than one cell along the wall of a pulmonary vein and block all potential paths for the signal out of the vein, in one particular exemplary procedure using a catheter.

FIGS. 22-24 illustrate an ablation catheter 38 employing a manifold 72 arrangement similar to that illustrated in FIGS. 3-10. Particularly, FIG. 22 is an isometric view of the ablation catheter, FIG. 23 is a section view taken along line 23-23 of FIG. 22, and FIG. 24 is a partial section view taken along line 24-24 of FIG. 22. The catheter includes a tubular body 50 defining a shaping wire lumen 114, an ablating fluid supply lumen 70, and an electrode lumen 80. The tubular body of the catheter may be precurved to form a loop shape at its distal end. The catheter of FIGS. 22-24 does not include a shaping element. However, the catheter may also employ a curved shaping element connected with the tubular body to impart a curve to the tubular body similar to that discussed with respect to FIGS. 3A-12.

Instead of a precurved tubular body, a straight body may include a pull wire 116 housed within the shaping wire lumen 114 that causes the tubular body to form the loop shape or other curved shape when a physician working with the catheter pulls on the pull wire. A pull wire may also be employed in a catheter arrangement having a curved body. In such a configuration, the physician performing a procedure may change the size and shape of the loop or other curved shape by pulling the wire. For example, in one configuration, the tubular body of the catheter may be precurved to take on a shape similar to that shown in FIGS. 4A-4C. When the catheter is pushed out of the sheath 40 it will then form a loop along the ablation region. Pulling on the wire will contract the loop into a smaller diameter such as is shown, for example, in FIGS. 3A-3C. In one implementation, the distal end of the pull wire is secured to the tip of the ablation catheter or to a side of the tubular body near the distal end. The proximal end of the pull wire extends outwardly from the proximal end of the tubular body of the catheter and is provided with a handle or other means by which a physician may grasp the pull wire in order to manipulate the shape of the catheter.

In embodiments of the ablation catheter that include a pull wire or shaping element, and either a precurved or uncurved tubular body, the pull wire 116 or shaping element 64 may be fabricated of a super elastic metal alloy material, such as a nickel-titanium alloy. One such suitable nickel-titanium alloy is commonly referred to as Nitinol. However, in some embodiments of the catheter, the pull wire need not be precurved as the shaft will be precurved. In such instances, the pull wire will be used to control the shape or circumference of the loop portion of the shaft so that it may be maneuvered into or adjacent different size veins.

Unlike the ablation catheter discussed with reference to FIGS. 3A-10, the manifold arrangement 72 of the catheter of FIGS. 22-24 is formed directly in the outer wall of the tubular body of the catheter. Recall, the manifold arrangement of FIGS. 3A-10 is formed in the shaping element. Referring now primarily to FIGS. 23 and 24, each manifold includes at least one inlet port 76 providing a fluid conduit between the fluid supply lumen 70 and the ablating fluid outlet port 78. Generally, the ablating fluid outlet port defines a larger opening than the inlet port(s). In one particular configuration, each manifold includes two inlet ports arranged generally transverse to the longitudinal axis of the fluid lumen.

An electrode 74 is housed within the electrode lumen 80. The electrode lumen is arranged such that the electrode is exposed to ablating fluid flowing within each manifold 72 during an ablation procedure. In one particular configuration, the electrode lumen is arranged generally parallel with the longitudinal axis of the catheter. The electrode lumen positions the electrode housed therein within the ablating fluid outlet port 78 of each manifold. The inlet ports 76 are arranged generally to each side of the electrode exposed within the ablating fluid port. Some amount of fluid flowing within the fluid supply lumen 70 will be diverted into the inlet ports of each manifold and past the electrode.

As with the manifolds of FIGS. 3-12, the manifolds of FIGS. 22-24 include channels 82 or slots extending away from each ablation fluid outlet port 78. When the ablation catheter is pressed against a target tissue 68, the channels provide an exit path (illustrated with arrows in FIG. 23) into the bloodstream for the saline flowing out of the ablating fluid port. Without a channel or some other exit path for the saline, the saline may be more readily blocked by the tissue and will not as readily flow through the manifold and across the electrode in order to ablate the target tissue. In one example, the channels are arranged such that some portion of at least one of the channels will extend away from the target tissue in order to provide at least one exit path for the saline flowing through the manifold.

In one particular configuration, the channels are sized to provide little resistance to saline flow, and minimize the diversion of electrical current from the target tissue. In such a configuration, the depth of the channel is about 0.005 inch and the width is about 0.003 inch adjacent the ablating fluid outlet port 78. The channels are defined in the outside circumference of the tubular side wall of the catheter. As such, the channels are curved with the depth of the channel tapered along its length. The deeper ends of the channel 80 are adjacent the ablating fluid outlet ports and the depth of the channel lessens as the channel extends away from the ablating fluid ports. From FIG. 23, it can be seen that due to the curvature of the channel, when the catheter is located against target tissue, the channel extends along and away from the target tissue. During a procedure, a portion of at least one channel associated with each ablating port should extend away from the target tissue. As such, a path for fluid to flow away from the electrode 74 is provided. In addition, the depth of the channel is larger than the width, which helps to prevent tissue from deforming into the channel and occluding the manifold when the ablation region is pressed into or situated against target tissue.

In some embodiments discussed herein, radiopaque tip markers are provided at the end of the catheter or along the length of the catheter so that a physician may track the progress of the catheter en route to target tissue and the placement of the catheter at the target tissue. In the ablation catheter of FIGS. 22-23, a coiled spring 118 is located with the fluid lumen 70 generally along the ablation region 42 of the catheter. In some examples, the coiled spring may be fabricated of platinum, tantalum, gold, stainless steel, gold-plated stainless steel, and the like to provide radiopacity.

The coiled spring 118 may be provided along any length of the catheter desired. In one particular configuration, the coiled spring is provided along the length of the ablation region. The coiled spring is easily deformable and flexible and thus conforms to the various curvatures of a catheter while it is being routed or steered to target tissue and while it is being maneuvered or shaped (e.g., formed into a loop) to perform an ablation procedure or other procedure.

Figure 25:
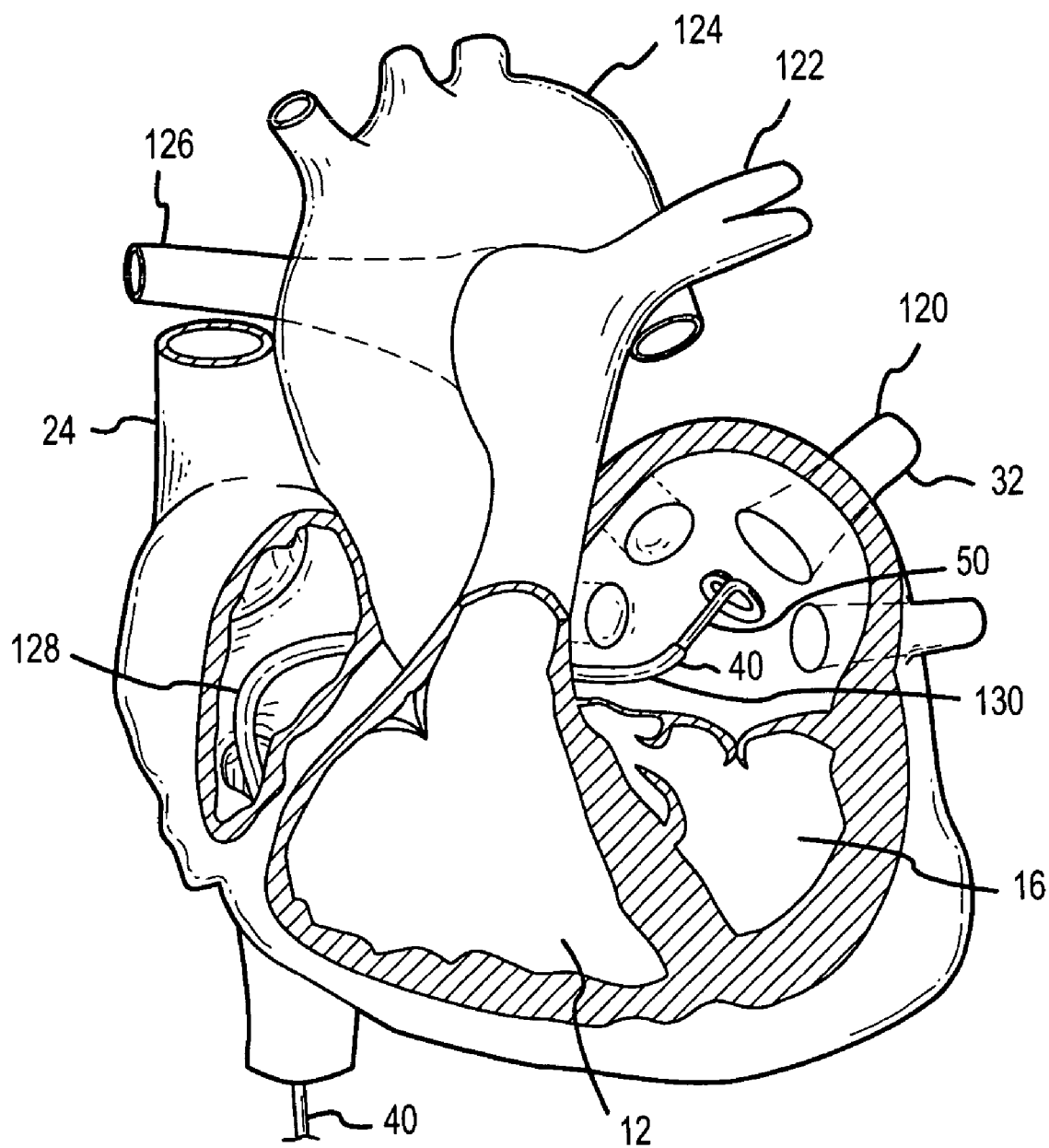
FIG. 25 is a partial cut away diagram of the human heart showing a sheath routed from the inferior vena cava, into the right atrium, through the interatrial septum, and into the left atrium, and with a shapable ablation catheter extending outwardly from the sheath in alignment with the left superior pulmonary vein.
Figure 26:
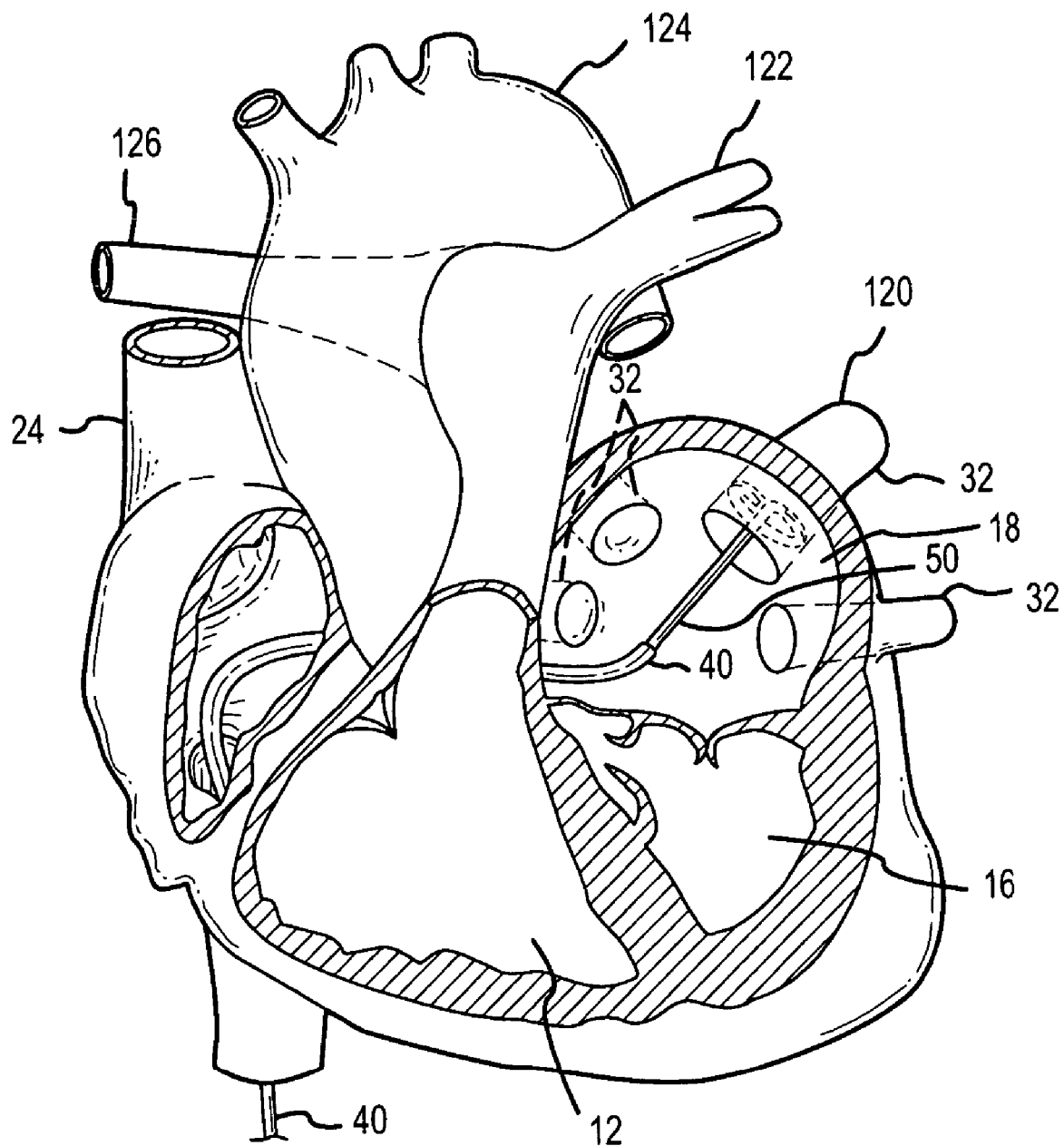
FIG. 26 is a partial cut away diagram of the human heart showing a sheath routed from the inferior vena cava, into the right atrium, through the septum, and into the left atrium, and with a shapable ablation catheter extending into the left superior pulmonary vein to form an ablation therein.

FIGS. 25 and 26 depict one ablation catheter according to the present invention while being used to ablate tissue in the left superior pulmonary vein 120. FIGS. 25 and 26 include a number of primary components of the heart (also shown in FIG. 1) to orient the viewer. In particular, starting in the upper left hand portion of FIGS. 25 and 26 and working around the periphery of the heart in a counterclockwise fashion, the following parts of the heart 10 are depicted: superior vena cava 24, right atrium 14, inferior vena cava 22, right ventricle 12, left ventricle 16, left superior pulmonary vein 94, left atrium 18, left pulmonary artery 122, arch of aorta 124, and right pulmonary artery 126. The distal portion 54 of the ablation catheter is positioned adjacent to the ostium 34 of the left superior pulmonary vein 120 using known procedures like the "Seldinger technique." For example, to get the distal loop portion 54 of the ablation catheter 38 in the position shown in FIG. 25, the right venous system may be first accessed using the "Seldinger technique," wherein a peripheral vein (such as a femoral vein) is punctured with a needle, the puncture wound is dilated with a dilator to a size sufficient to accommodate an introducer. The introducer with at least one hemostatic valve is seated within the dilated puncture wound while maintaining relative hemostasis. With the introducer in place, the sheath with a dilator and needle housed within the lumen are introduced through the hemostatic valve of the introducer and advanced along the peripheral vein, into the region of the vena cava (e.g., the inferior vena cava 22), and into the right atrium 14. From there, the sheath 40 is further advanced through a hole in the interatrial septum, which a doctor would make using the needle and dilator. Once the sheath is fit through the interatrial septum and gains access to the left atrium 18, the sheath is positioned generally along the longitudinal axis of one of the pulmonary veins. In FIG. 25, the sheath 40 is shown in alignment with the longitidunial axis of the left superior pulmonary vein 120. Positioned as such, the dilator and needle are pulled back through the sheath.

To facilitate the proper positioning of the sheath within the left atrium, in one particular implementation, the sheath is preset with a curvature defined to assist in maneuvering the sheath to the correct position within the heart. The curvature will depend on the location within the heart in which the catheter will be guided for the ablation procedure. In the example of an ablation procedure within the left atrium 18 and in proximity or within one of the pulmonary veins 32, the sheath is preset with a complex three dimensional curve with a first section 128 corresponding with the turn between the inferior vena cava 22 toward the septum and with a second section 130 corresponding with the curve between the septum and one of the pulmonary veins. The curve in the sheath may be set by heating up the sheath on a die. The die defines the desired curvature, and heating the sheath on the die sets the curve in the sheath.

To properly guide the ablation catheter 38 to the appropriate location, other guiding systems may be employed, such as rails, precurved guiding introducers, guidewires, and the like. For example, the ablation catheter may be properly guided within the heart with a guiding introducer system including one or more guiding introducers and a rail and ablation catheter system as described in U.S. Pat. No. 6,120,500, titled "Rail Catheter Ablation and Mapping System," which is hereby incorporated by reference in its entirety as though fully set forth herein. In another example, the ablation catheter may be properly guided within the heart using a guidewire such as is described in U.S. Pat. No. 5,162,911, titled "Over-the-wire catheter," which is hereby incorporated by reference it its entirety as though fully set forth herein.

After the sheath is properly positioned and the dilator is removed, the ablation catheter is fed through the lumen and out the distal end of the sheath. In an embodiment of the ablation catheter that is precurved to provide a looped area 54, upon exiting the sheath the ablation catheter further assumes its precurved shape. As shown in FIG. 25, the plane defined by the looped portion of the shaft will be generally perpendicular to the longitudinal axis of the target pulmonary vein after the shaft exits the sheath.

Prior to insertion of the looped portion 54 of the catheter 38 into a pulmonary vein, the catheter is unactuated, such as is shown in FIGS. 3A-C. In FIG. 24, the distal looped portion of the ablation catheter has been inserted into the left superior pulmonary vein and fluid is introduced into the actuating lumen 50 so that the loop extends outwardly and orients the ablation region 42 adjacent the walls of the pulmonary vein, i.e. the target tissue. Referring to the ablation catheter discussed with respect to FIGS. 5-8, while an ablation catheter is in the pulmonary vein as depicted in FIG. 26, fluid is introduced into the second lumen 70 and the electrode 74 is energized so that fluid flowing through the manifolds 72 carry ablation energy to the vein to create the desired lesion. Referring again to FIG. 8, ablation energy passes through the conductive medium flowing out the ablation ports 78 and past the electrode strands 74 and into the target tissue. The tissue experiences ohmic heating due to the energy conducted into the target tissue. Thus, a lesion is formed in the target tissue by the energy passing through the conductive medium. The conductive medium also dilutes the blood around the ablation catheter.

In order to form a sufficient lesion, it is desirable to raise the temperature of the tissue to at least 50° C. for an appropriate length of time (e.g., one minute). Besides ablating the tissue, the conductive medium flowing through the ports 70 prevents blood from flowing into the ablation catheter and pushes blood from the area adjacent to the ports. This helps prevent coagulum, which can have undesirable effects on the patient. The conductive medium is also caused to flow at a rate that prevents the electrode from overheating the conductive medium producing vapor in the fluid lumen 70. Thus, the flow of conductive medium through the fluid lumen and out the ports is managed or regulated so that there is sufficient flow to prevent vaporization, but not so much flow that the electrode is prohibited from sufficiently heating the fluid to form a desired lesion. Also, if too much conductive medium flows out of the ports, the hemodynamics of the patient may be adversely affected by the excess quantity of conductive medium being mixed with the patient's blood. The desired flow rate is achieved by adjusting the pressure driving the conductive medium through the fluid lumen, the diameter of the ports, and the spacing between the ports.

FIGS. 27A-27D are representative section views of the ablation catheter 38 positioned within or adjacent to one of the pulmonary veins. Collectively, these figures illustrate the flexible resilient nature of the ablation catheter, and the way it way be positioned to provide a circumferential lesion within differently shaped veins or within differently shaped portions of veins. Such shapes may be achieved with a curved or partially curved tubular body ablation catheter shaft with or without the assistance of a shaping element.

In the example of an ablation catheter that includes a partially precurved shaft and a shaping element, upon exiting the sheath, the catheter forms a first loop shape. By introducing fluid into the actuating lumen 56, the loop may be expanded, i.e., the diameter of the loop increased, so that the ablation region may be expanded to contract the walls of a vein or the like. To retract the ablation catheter, the fluid pressure in the actuating lumen is lessened to decrease the loop size and withdraw the ablation catheter out of the vein.

Although preferred embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

I claim:

1. An ablation catheter comprising:
   a tubular body having a circumference, at least one actuating lumen sealed at a first end and open to fluid flow at a second end, and a distal end region, the tubular body defining at least a partial curve along the distal end region of the tubular body, the partial curve being adapted to change curvature when a fluid pressure in the at least one actuating lumen changes; and
   at least one ablating electrode arranged along the at least partial curve, the at least one electrode being adapted to change curvature along with the at least partial curve along the distal end region of the tubular body;
   the tubular body further comprising at least one ablation fluid supply lumen extending through the at least partial curve of the distal end region and including at least one manifold to permit a fluid to exit the at least one ablation fluid supply lumen,
   wherein the at least one manifold includes at least one manifold inlet port in fluid communication with an ablating fluid outlet port, the ablating fluid outlet port having a larger cross-sectional area than the at least one manifold inlet port, and
   wherein the at least one electrode is configured to be flexible and resilient, and wherein the at least one electrode extends around only a portion of the circumference of the tubular body.

2. The ablation catheter of claim 1 further comprising a flexible and resilient shaping element.

3. The ablation catheter of claim 1 wherein the at least one flexible and resilient electrode is comprised, at least partially, of material selected from the group consisting of platinum, gold, stainless steel, and composite of conductive polymer metal.

4. The ablation catheter of claim 1 wherein the at least one electrode defines a saw tooth pattern.

5. The ablation catheter of claim 1 wherein the at least partial curve defines an outside radius, and wherein the at least one electrode defines a first end region and a second end region, and wherein the first end region is coupled with a point along the outside radius of the at least partial curve and wherein the second end region is coupled with a second point along the outside radius of the at least partial curve along the distal end region of the tubular body.

6. The ablation catheter of claim 1 wherein the at least one electrode further defines an elastically deformable electrode.

7. The ablation catheter of claim 6 wherein the at least one elastically deformable electrode is biasedly coupled with the at least partial curve along the distal end region of the tubular body.

8. The ablation catheter of claim 7 wherein the biased connection of the at least one elastically deformable electrode is biased to change the curvature of the at least partial curve along the distal end region of the tubular body.

9. The ablation catheter of claim 1 wherein the at least partial curve along the distal end region of the tubular body defines a closed loop.

10. The ablation catheter of claim 1 wherein the at least partial curve along the distal end region of the tubular body defines an open loop.

11. The ablation catheter of claim 1 wherein the at least one electrode includes at least one electrode strand interlaced along the at least partial curve along the distal end region of the tubular body.

12. The ablation catheter of claim 11 wherein the at least partial curve defines an outside surface, and wherein the at least one electrode strand is interlaced along the outside surface.

13. The ablation catheter of claim 11 wherein the at least partial curve defines an inside surface, and wherein the at least one electrode strand is interlaced along the inside surface.

14. The ablation catheter of claim 12 wherein the at least one electrode strand is interlaced along the outside circumference such that the electrode strand is intermittently exposed along the outside circumference.

15. The ablation catheter of claim 14 wherein:
    the at least one electrode strand defines a first length of the at least one strand, the first length defining intermittently exposed sections of the at least one electrode strand; and
    the at least one electrode strand further defines a second length of the at least one strand, the second length defining intermittently exposed sections of the at least one electrode strand.

16. The ablation catheter of claim 15 wherein the first length of the at least one strand and the second length of the at least one strand cooperate to define a generally continuously exposed segment of the at least one strand.

17. The ablation catheter of claim 16 wherein the generally continuously exposed segment of the at least one strand is coupled with a power supply and adapted to be energized thereby during an ablation procedure.

18. The ablation catheter of claim 1, wherein the at least one manifold further comprises a fluid channel extending away from the ablating fluid outlet port in a direction substantially perpendicular to a direction in which the at least one ablating electrode is arranged.

19. An ablation catheter comprising
    a tubular shaft having a circumference and defining a distal end region, the tubular shaft further defining at least a partial curve along the distal end region;
    the tubular shaft defining at least one lumen including at least one manifold located along the at least a partial curve to permit a fluid flowing within the at least one lumen to exit the tubular shaft through the at least one manifold; and
    flexible and resilient electrode means for conveying ablation energy to a target tissue, the flexible and resilient electrode means arranged along the at least partial curve along the distal end region of the tubular shaft and extending around only a portion of the circumference of the tubular shaft,
    wherein the at least one manifold includes at least one manifold inlet port in fluid communication with an ablating fluid outlet port, the ablating fluid outlet port having a larger cross-sectional area than the at least one manifold inlet port.

20. The ablation catheter of claim 19 wherein the means for conveying ablation energy to a target tissue comprises at least one electrode arranged in a flexible and resilient configuration along some portion of the at least partial curve along the distal end region of the tubular shaft.

* * * * *